(12) United States Patent
Long et al.

(10) Patent No.: US 6,210,389 B1
(45) Date of Patent: Apr. 3, 2001

(54) FASTENER SYSTEM WITH A LIFT REGION

(75) Inventors: Andrew Mark Long, Appleton; Patrick Robert Lord, Neenah; Brian Keith Nortman; Paula Kay Zoromski, both of Appleton, all of WI (US); Richard John Schmidt, Roswell; Mari-Pat Yvonne Von Feldt, Atlanta, both of GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/154,961

(22) Filed: Sep. 17, 1998

(51) Int. Cl.$^7$ ................ A61F 13/15; A44B 1/04
(52) U.S. Cl. ............ 604/391; 604/390; 24/442; 24/450; 24/452
(58) Field of Search ............. 24/442, 450, 452; 604/391, 390

(56) References Cited

U.S. PATENT DOCUMENTS

| | | | |
|---|---|---|---|
| 3,893,460 | * | 7/1975 | Karami ................. 128/287 |
| 3,901,236 | | 8/1975 | Assarsson et al. ........ 128/284 |
| 3,937,221 | * | 2/1976 | Tritsch ................. 128/287 |
| 4,076,663 | | 2/1978 | Masuda et al. ........ 260/17.4 GC |
| 4,286,082 | | 8/1981 | Tsubakimoto et al. ........ 526/240 |

(List continued on next page.)

FOREIGN PATENT DOCUMENTS

| | | | |
|---|---|---|---|
| 0 217 032 A2 | 4/1987 | (EP) | ............ D04H/13/00 |
| 0 233 704 B1 | 8/1987 | (EP) | ............ A61F/5/44 |
| WO 98/10728 A1 | 3/1998 | (WO) | ............ A61F/13/58 |

OTHER PUBLICATIONS

American Society for Testing Materials (ASTM) Designation: D 5169–91, "Standard Test Method for Shear Strength (Dynamic Method) of Hook and Loop Touch Fasteners," pp. 687–689, published Nov. 1991.

American Society for Testing Materials (ASTM) Designation: D 5170–91, "Standard Test Method for Peel Strength ("T" Method) of Hook and Loop Touch Fasteners," pp. 690–692, published Nov. 1991.

Federal Test Method Standard (FTMS) No. 191A, Method 5514, "Water Resistance of Cloth; Low Range, Hydrostatic Pressure Method," Jul. 20, 1978, 3 pages.

TAPPI Official Test Method T 543 om–94, "Bending Resistance of Paper (Gurley Type Tester)," published by the TAPPI Press, Atlanta, Georgia, pp. 1–5.

*Primary Examiner*—John G. Weiss
*Assistant Examiner*—Paul Shanoski
(74) *Attorney, Agent, or Firm*—Paul Yee

(57) ABSTRACT

An article (10) has a lengthwise longitudinal direction (26), a lateral cross-direction (24), a first article portion (12), a second article portion (14), and a fastener (36) for securing the first article portion (12) to the second article portion (14). The fastener (36) includes at least one first fastener component (70) attached to a lateral side section (86) of the first article portion (12), and a cooperating, second fastener component (72) attached to the second article portion (14). The first fastener component includes an engagement substrate (56) having an appointed lift region (54), and a plurality of engagement members (40), such as the representatively shown hook members, which are operably attached to extend away from the engagement substrate. The lift region (54) is disposed along at least a longitudinally extending, outboard edge of the engagement substrate (56), and the lift region contains a plurality of engagement members which have been substantially deactivated.

20 Claims, 11 Drawing Sheets

U.S. PATENT DOCUMENTS

| | | | |
|---|---|---|---|
| 4,290,174 | * | 9/1981 | Kalleberg ............................... 24/204 |
| 4,322,875 | * | 4/1982 | Brown et al. ......................... 24/204 |
| 4,662,037 | * | 5/1987 | Provost et al. ....................... 24/447 |
| 4,663,220 | | 5/1987 | Wisneski et al. ................... 428/221 |
| 4,699,823 | | 10/1987 | Kellenberger et al. ............. 428/219 |
| 4,704,116 | | 11/1987 | Enloe ............................... 604/385 A |
| 4,753,646 | | 6/1988 | Enloe ............................... 604/385 R |
| 4,916,005 | | 4/1990 | Lippert et al. ...................... 428/192 |
| 4,938,753 | | 7/1990 | Van Gompel et al. ........... 604/385.2 |
| 5,019,073 | | 5/1991 | Roessler et al. ..................... 604/391 |
| 5,040,275 | * | 8/1991 | Eckhardt et al. ...................... 24/447 |
| 5,226,992 | | 7/1993 | Morman .............................. 156/62.4 |
| 5,288,546 | | 2/1994 | Roessler et al. ..................... 428/284 |
| 5,304,162 | * | 4/1994 | Kuen ................................... 604/391 |
| 5,374,262 | * | 12/1994 | Kuen, Jr. et al. .................... 604/391 |
| 5,386,595 | * | 2/1995 | Kuen et al. ............................. 2/400 |
| 5,399,219 | | 3/1995 | Roessler et al. ..................... 156/259 |
| 5,423,789 | * | 6/1995 | Kuen ................................... 604/386 |
| 5,486,166 | | 1/1996 | Bishop et al. ....................... 604/366 |
| 5,490,846 | | 2/1996 | Ellis et al. ........................... 604/366 |
| 5,540,796 | | 7/1996 | Fries ..................................... 156/164 |
| 5,562,650 | | 10/1996 | Everett et al. ....................... 604/378 |
| 5,595,618 | | 1/1997 | Fries et al. ........................... 156/164 |
| 5,605,735 | | 2/1997 | Zehner et al. ....................... 428/100 |
| 5,606,781 | * | 3/1997 | Provost et al. ......................... 24/452 |
| 5,624,429 | | 4/1997 | Long et al. .......................... 604/391 |
| 5,858,515 | | 1/1999 | Stokes et al. ........................ 428/195 |
| 5,897,546 | * | 4/1999 | Kido et al. ........................... 604/391 |
| 5,933,927 | * | 8/1999 | Miller et al. ........................... 24/452 |

* cited by examiner

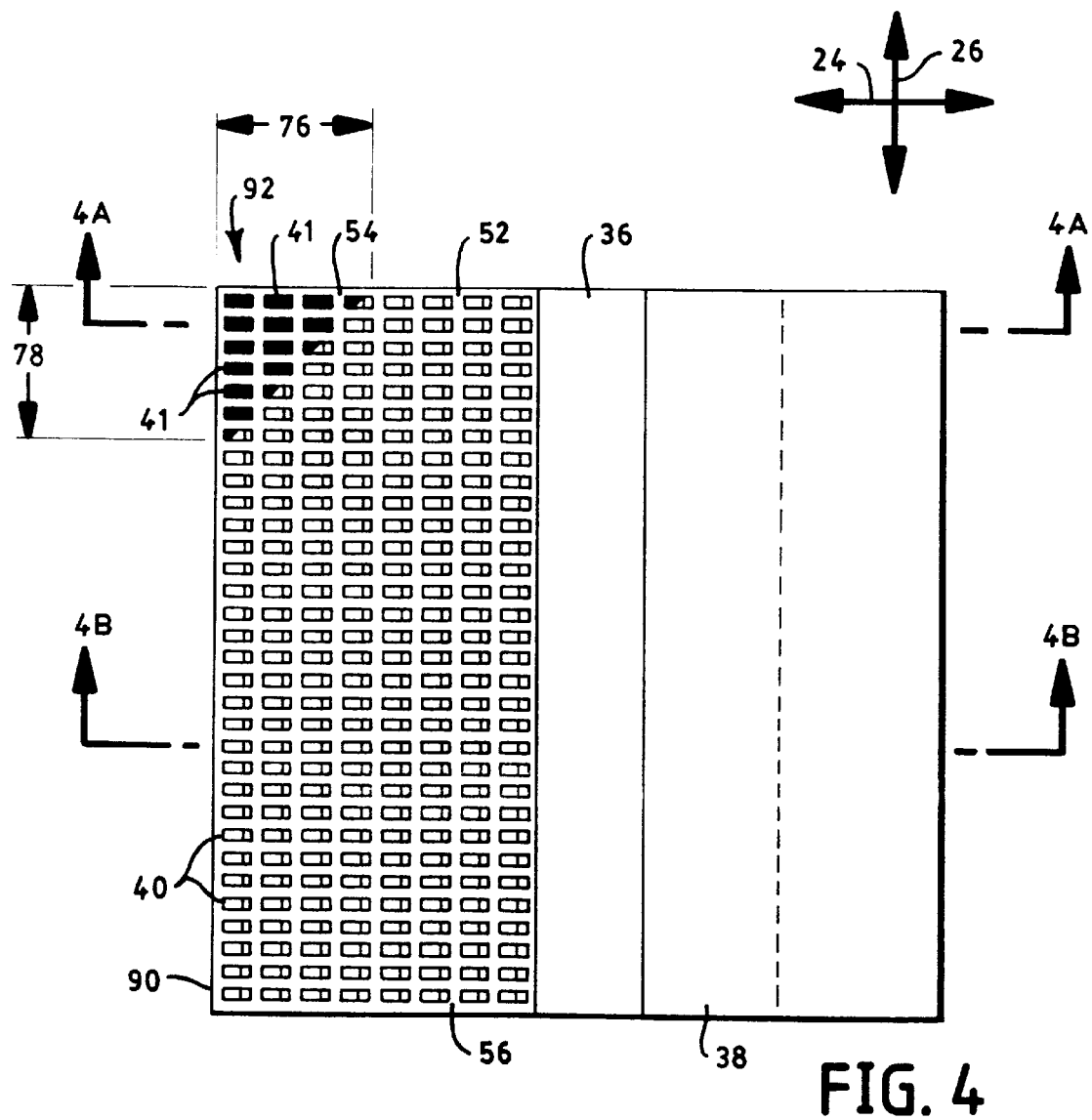
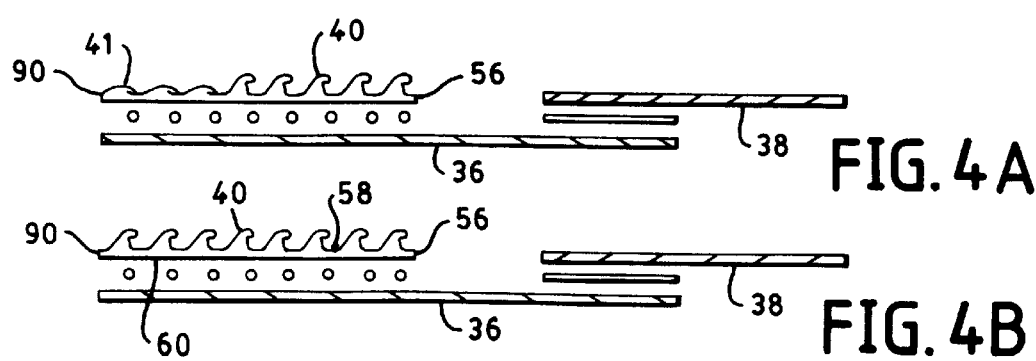
FIG. 4
FIG. 4A
FIG. 4B

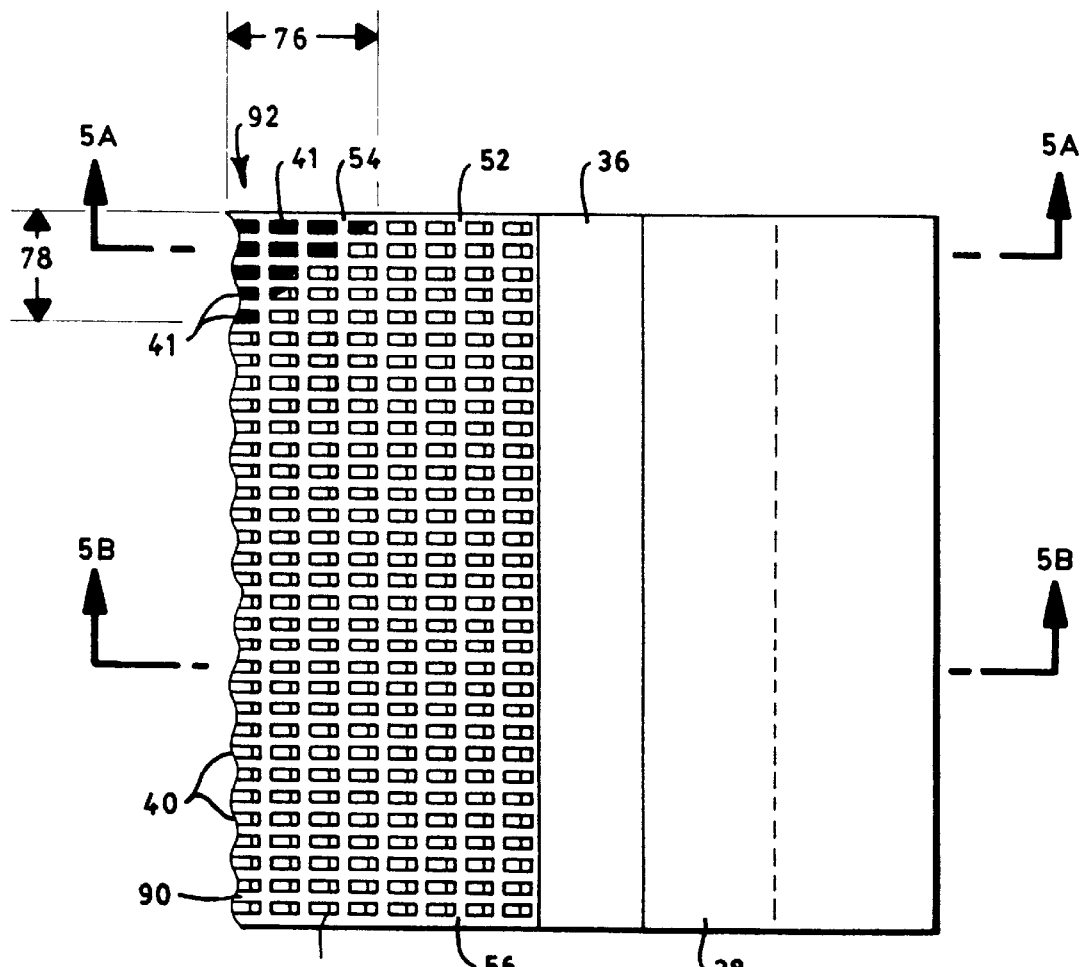
FIG. 5
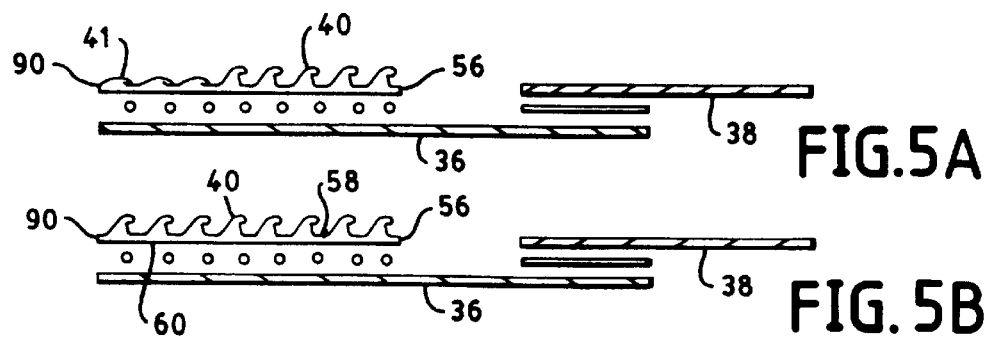
FIG. 5A
FIG. 5B

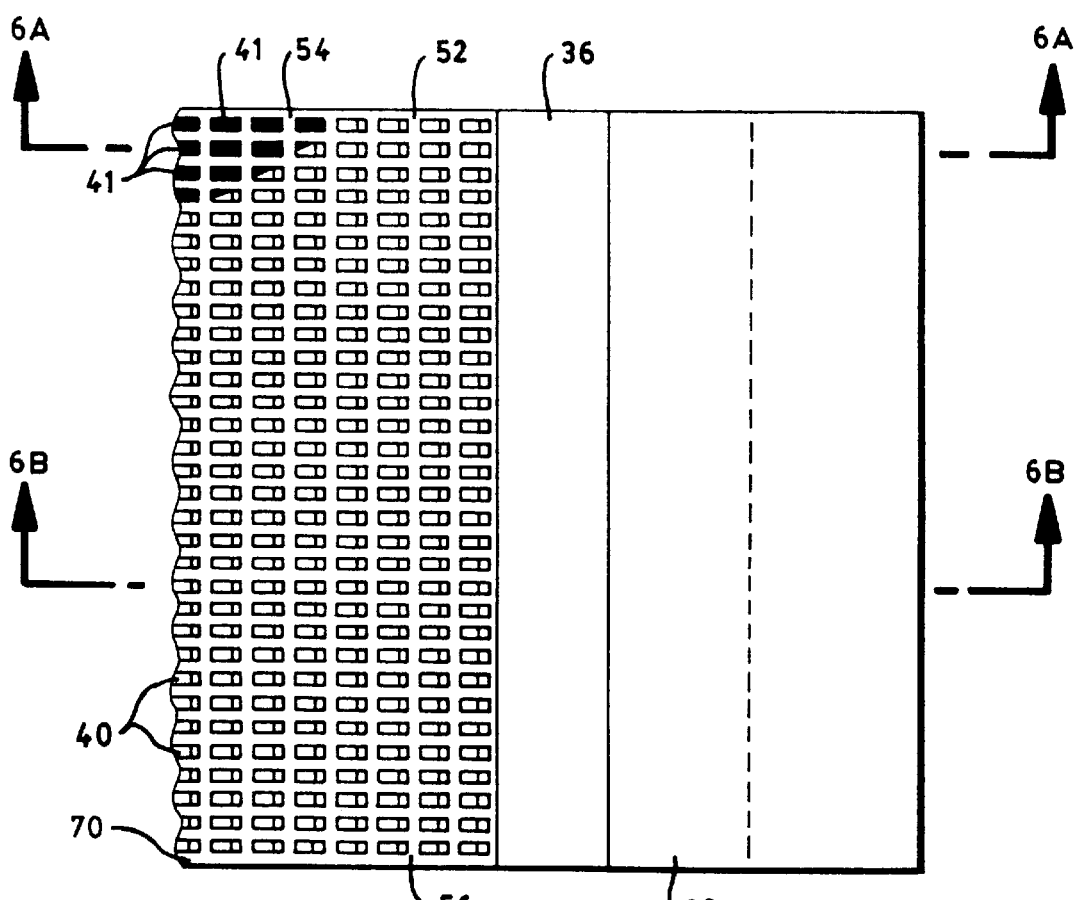
FIG. 6
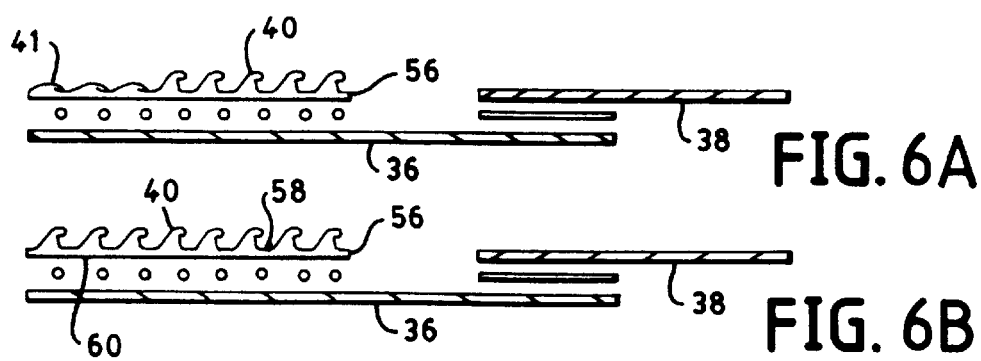
FIG. 6A
FIG. 6B

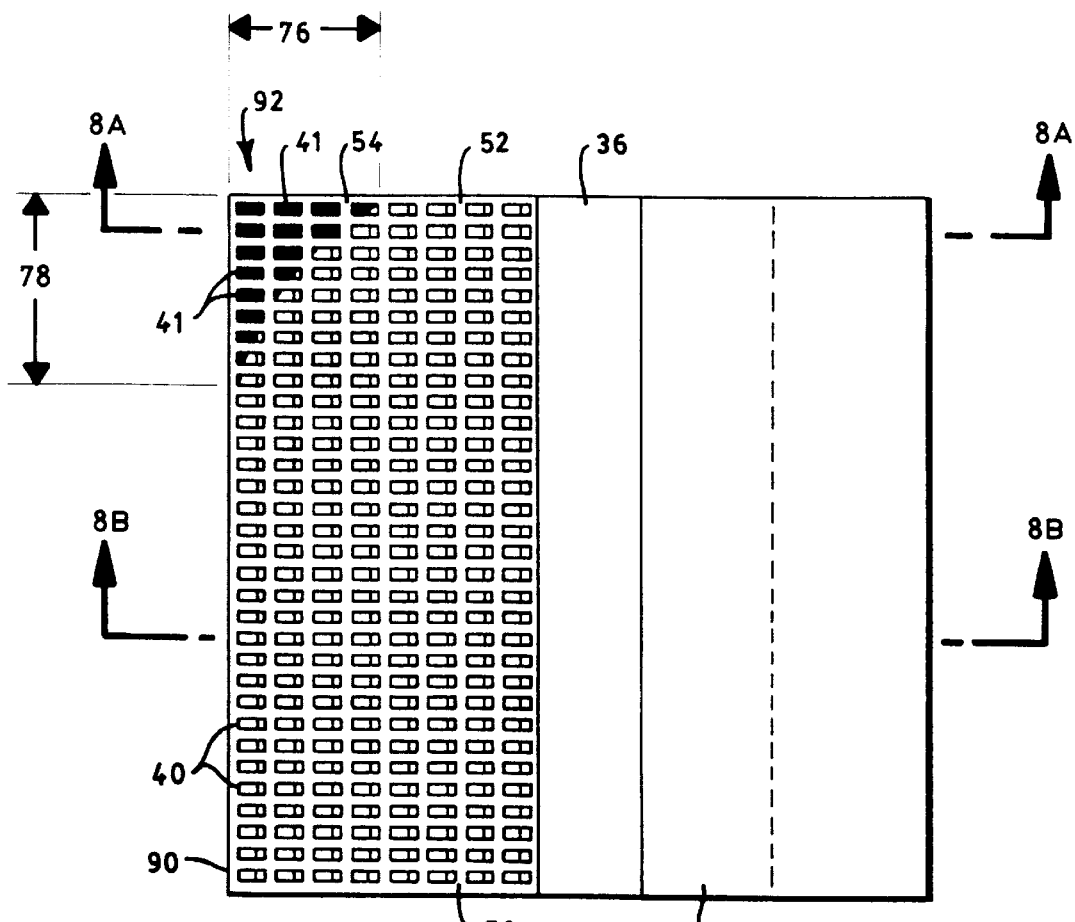
FIG. 8
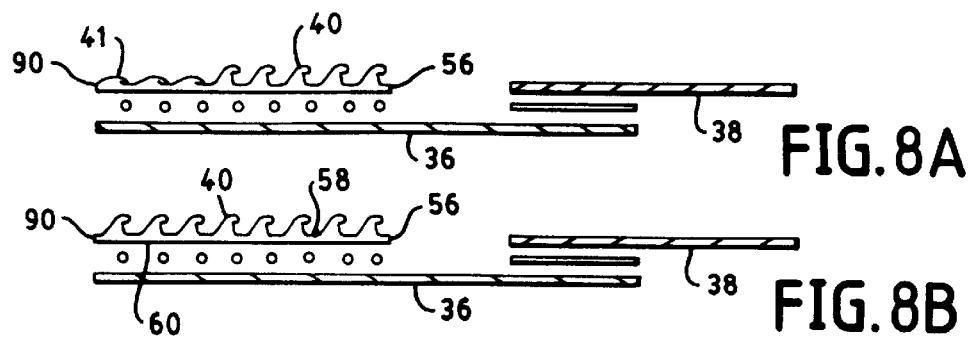
FIG. 8A
FIG. 8B

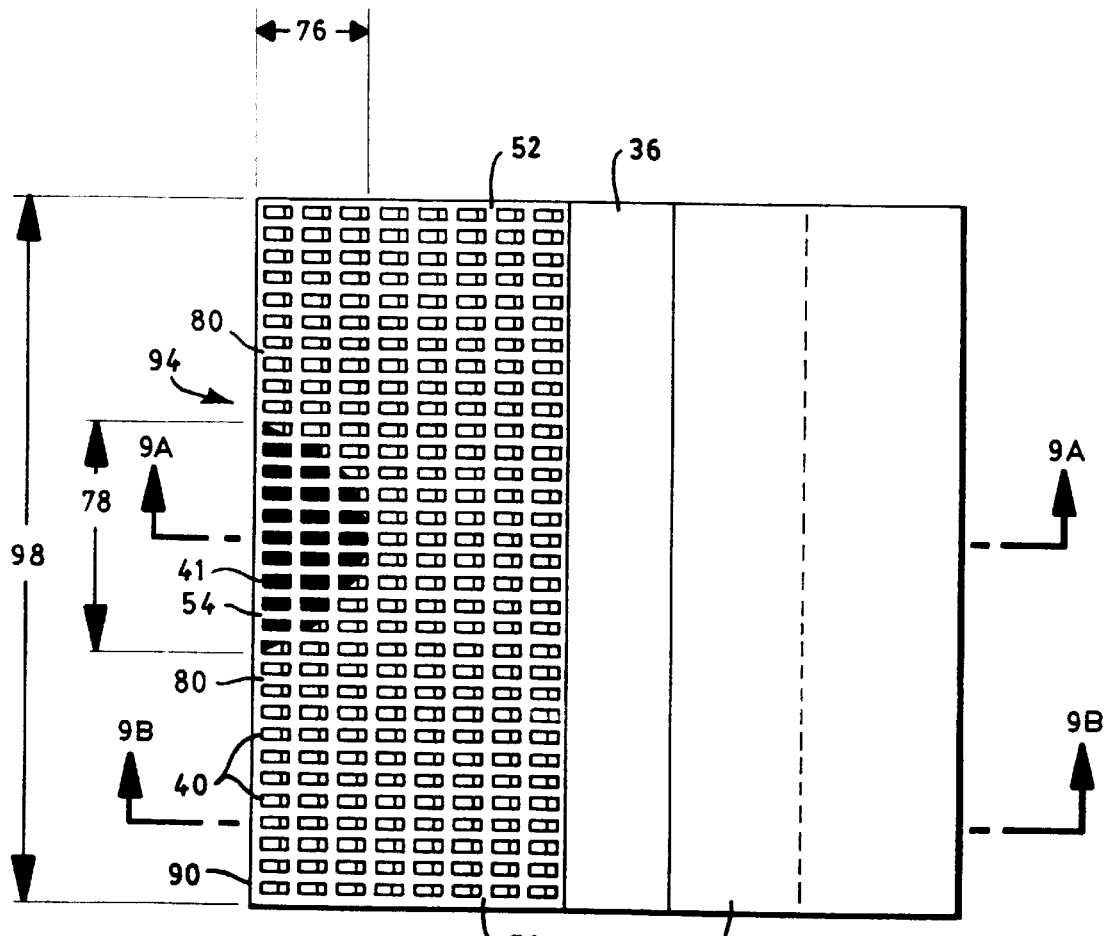
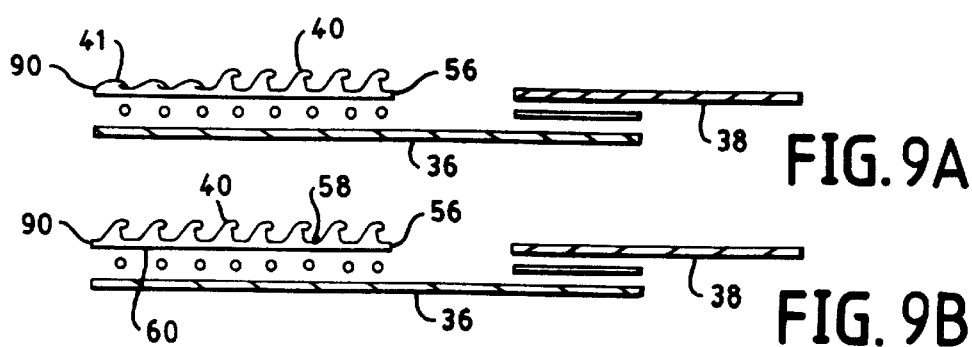
FIG. 9
FIG. 9A
FIG. 9B

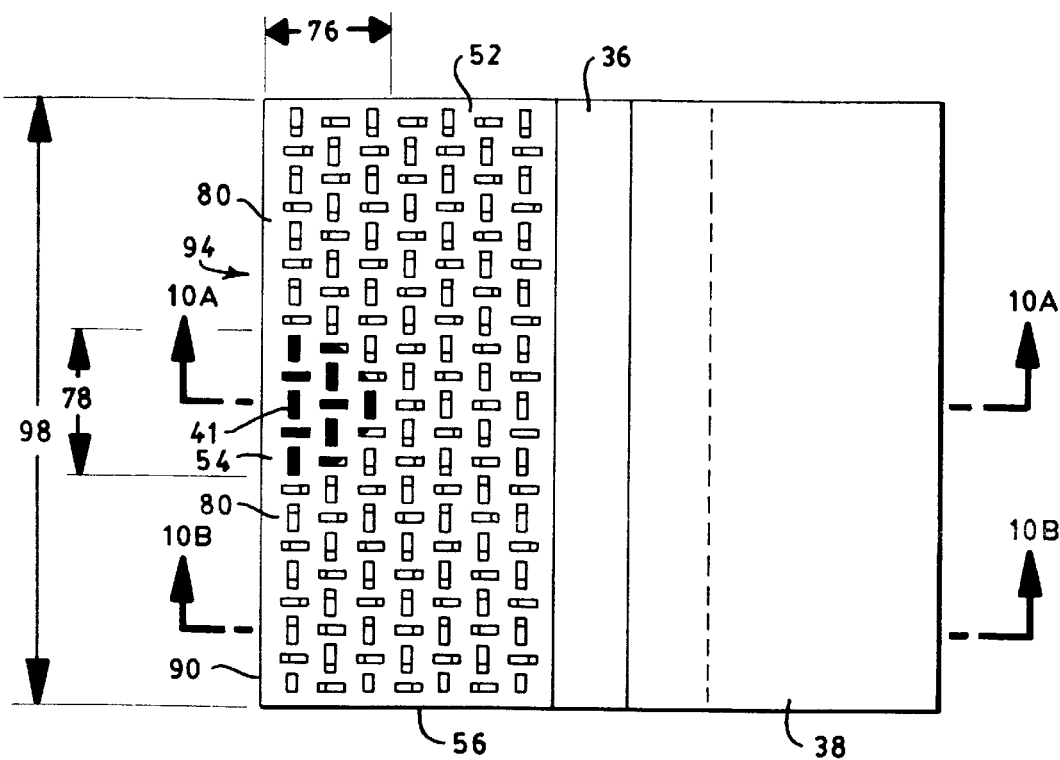
FIG. 10
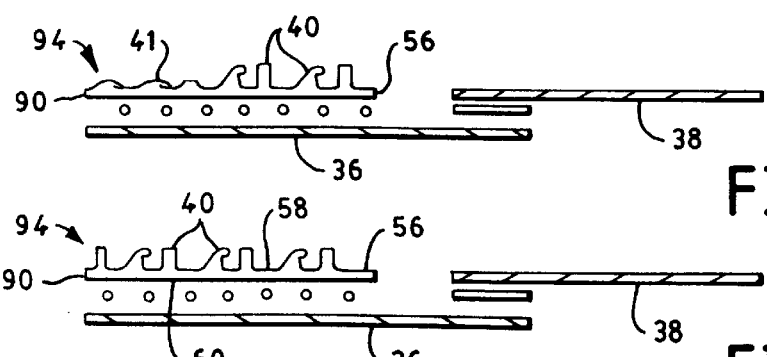
FIG.10A
FIG.10B

FASTENER SYSTEM WITH A LIFT REGION

FIELD OF THE INVENTION

The present invention relates to fastening systems for garments and other articles. More particularly, the present invention relates to interlocking, mechanical-type fastening systems which can be employed with disposable articles, such as gowns, diapers, incontinence garments and the like.

BACKGROUND OF THE INVENTION

Conventional disposable absorbent articles have typically employed adhesive fastening tapes for securing the article on a wearer. Such articles have also been constructed with interengaging mechanical fasteners, such as VELCRO brand hook-and-loop fasteners. Particular articles have included a fastening system which has extended along substantially the entire length of an ear section of the article. Other fastening systems have included strips or segmented sections of adhesive. Still other systems have included strips or segmented sections of selected mechanical fastener components, such as individual sections of hook material. In addition, various types of hook materials, such as inverted-J shaped, T-shaped and generally mushroom-shaped hooks have been employed. Conventional fastening systems have also employed tapered fastening tabs where the attaching area on the user's end is relatively wide at its region adjacent the longitudinally extending sides of the diaper, and is tapered to a more narrow width at its more remote distal end. For example, see European patent EP 0 233 704 B1 of H. Burkhard et al. Conventional fasteners have also included a finger tab region which remains relatively unattached during the fastening operation, and allows an easy grasping for detaching the fastener from its fastening engagement. Conventional fasteners and fastening systems, such as those described above, have not provided a desired combination of reliable securement, ease of unfastening, and ease of manufacture. The conventional fastening systems have not provided a sufficient capability to accommodate the stresses imposed by fastening the article on a wearer, while accommodating the other stresses and displacements caused by a moving wearer and also providing a desired ease of selective unfastening and removal. As a result, the conventional fastening systems have not provided desired levels of comfort, securement, ease and low cost of manufacture and ease of use.

BRIEF DESCRIPTION OF THE INVENTION

Generally stated, the present invention provides an article having a lengthwise longitudinal direction, a lateral cross-direction, a first article portion, a second article portion, and a fastener for securing the first article portion to the second article portion. The fastener includes at least one first fastener component attached to a lateral side section of the first article portion, and a cooperating, second fastener component attached to the second article portion. The first fastener component includes an engagement substrate having an appointed lift region, and a plurality of engagement members which are operably attached to extend away from the engagement substrate. The lift region is disposed along at least a longitudinally extending, outboard edge of the engagement substrate, and the lift region contains a plurality of engagement members which have been substantially deactivated.

In particular aspects of the invention, the engagement substrate may include an outboard, distal corner portion, and said lift region can be positioned at the outboard corner portion.

In other aspects of the invention, the engagement substrate may include a laterally outboard, distal border portion, and the lift region can be located at a medial section of the outboard border portion.

The incorporation of the various aspects of the fastening system of the invention can provide improved securement with greater resistance to premature pop-opens, and can also help provide improved fit, greater comfort, and reduced irritation of the wearer's skin. The distinctively configured engagement zones and finger lift tab regions can provide an improved combination of high engagement areas for greater securement and fastener reliability, and distinctively configured areas of relatively lesser engagement for ease of unfastening and removal of the article from a wearer and for reduced irritation of the wearer.

BRIEF DESCRIPTION OF THE DRAWINGS

The present invention will be more fully understood and further advantages will become apparent when reference is made to the following detailed description of the invention and the drawings, in which:

FIG. 4 representatively shows a top view of a side panel and a fastening tab assembly of the invention;

FIG. 4A representatively shows a schematic, laterally extending, expanded edge view along line 4A—4A of the fastening tab assembly illustrated in FIG. 4;

FIG. 4B representatively shows a schematic, laterally extending, expanded edge view along line 4B—4B of the fastening tab assembly illustrated in FIG. 4;

FIG. 5 representatively shows a top view of a side panel and a fastening tab assembly of the invention having curvilinear, wavy side edge and a corner lift region;

FIG. 5A representatively shows a schematic, laterally extending, expanded edge view along line 5A—5A of the fastening tab assembly illustrated in FIG. 5;

FIG. 5B representatively shows a schematic, laterally extending, expanded edge view along line 5B—5B of the fastening tab assembly illustrated in FIG. 5;

FIG. 6 representatively shows a top view of another side panel and a fastening tab assembly of the invention having another curvilinear, wavy side edge and a corner lift region;

FIG. 6A representatively shows a schematic, laterally extending, expanded edge view along line 6A—6A of the fastening tab assembly illustrated in FIG. 6;

FIG. 6B representatively shows a schematic, laterally extending, expanded edge view along line 6B—6B of the fastening tab assembly illustrated in FIG. 6;

FIG. 8 representatively shows a top view of another assembly of the side panel joined with another fastening tab of the invention having a corner lift region with a curvilinear inboard edge;

FIG. 8A representatively shows a schematic, laterally extending, expanded edge view along line 8A—8A of the fastening tab assembly illustrated in FIG. 8;

FIG. 8B representatively shows a schematic, laterally extending, expanded edge view along line 8B—8B of the fastening tab assembly illustrated in FIG. 8;

FIG. 9 representatively shows a top view of a side panel and a fastening tab assembly of the invention having an indented-type lift region which is bracketed by engagement members;

FIG. 9A representatively shows a schematic, laterally extending, expanded edge view along line 9A—9A of the fastening tab assembly illustrated in FIG. 9;

FIG. 9B representatively shows a schematic, laterally extending, expanded edge view along line 9B—9B of the fastening tab assembly illustrated in FIG. 9;

FIG. 10 representatively shows a top view of a side panel joined with another fastening tab assembly of the invention having an indented-type lift region and a mixed orientation of engagement members;

FIG. 10A representatively shows a schematic, laterally extending, expanded edge view along line 10A—10A of the fastening tab assembly illustrated in FIG. 10;

FIG. 10B representatively shows a schematic, laterally extending, expanded edge view along line 10B—10B of the fastening tab assembly illustrated in FIG. 10;

DETAILED DESCRIPTION OF THE INVENTION

The various aspects and embodiments of the invention will be described in the context of a disposable absorbent article, such as a disposable diaper. It is, however, readily apparent that the present invention could also be employed with other articles, such as caps, gowns, shoe covers, feminine care articles, children's training pants, incontinence garments and the like. Typically, the disposable articles are intended for limited use and are not intended to be laundered or otherwise cleaned for reuse. A disposable diaper, for example, is discarded after it has become soiled by the wearer.

Figure 1:
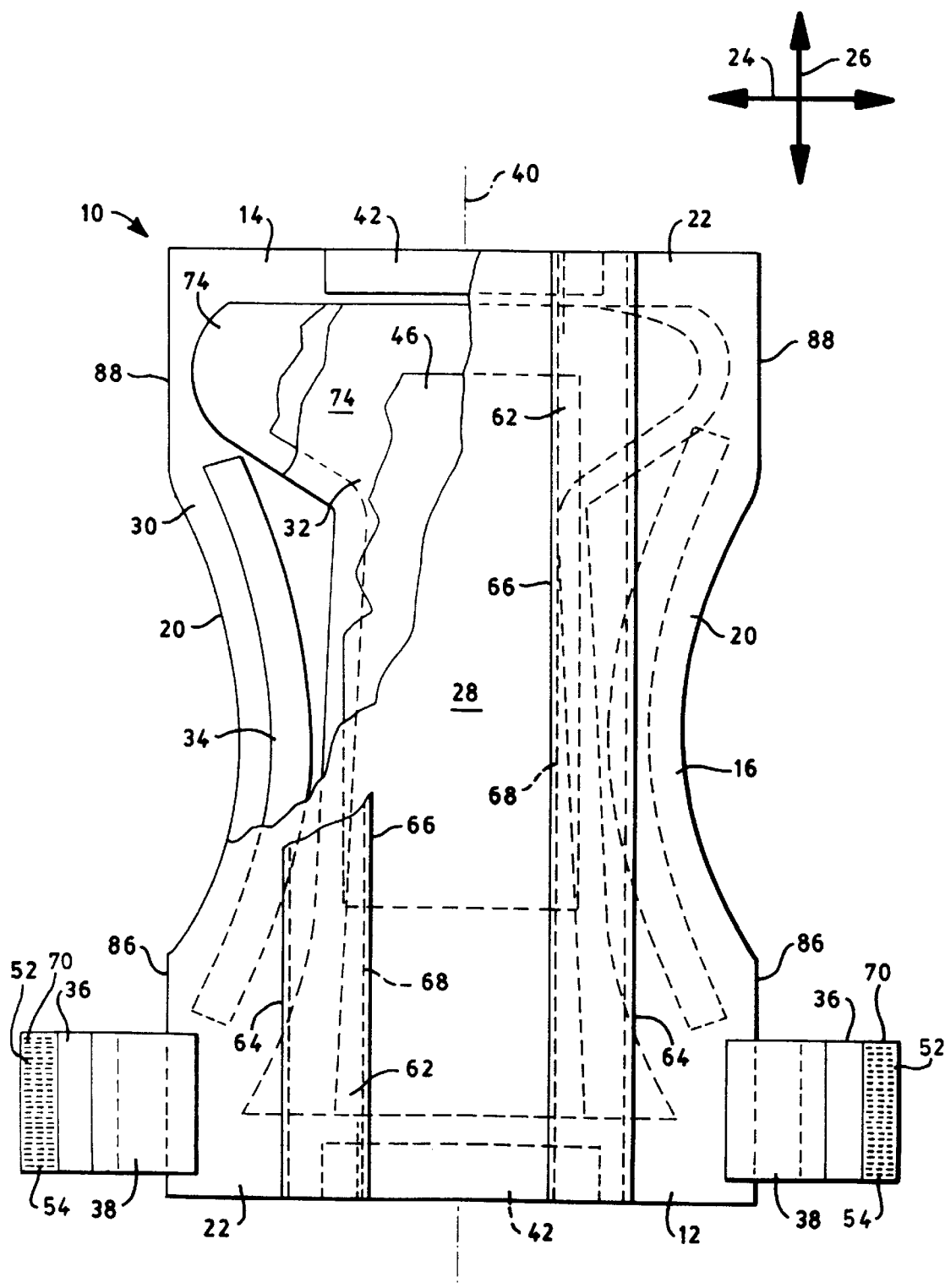
FIG. 1 representatively shows a partially cut-away, top view of a diaper article which incorporates the fastening system of the invention.
Figure 2:
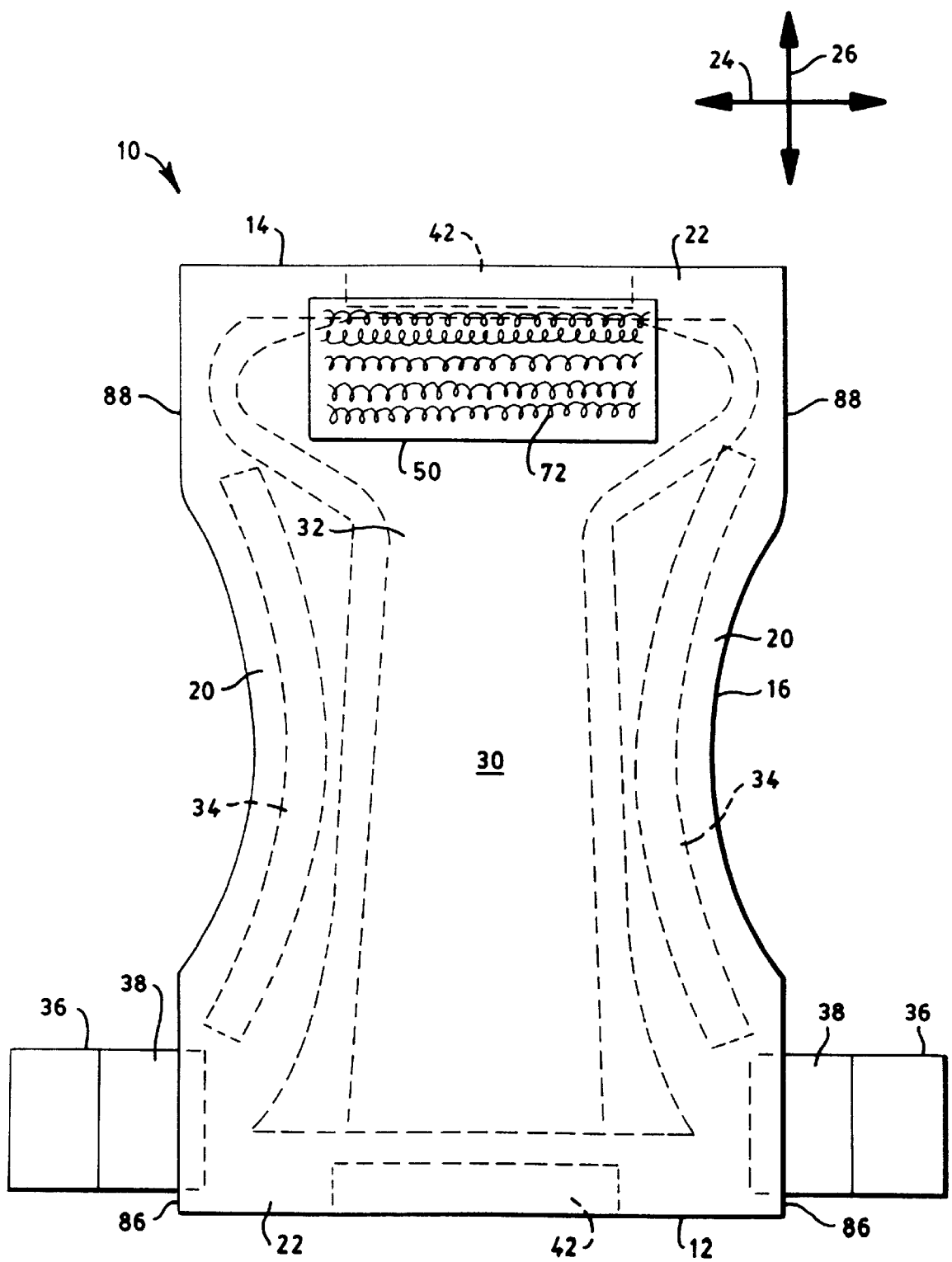
FIG. 2 representatively shows a plan view of the outward side of the article illustrated in FIG. 1.
Figure 3:
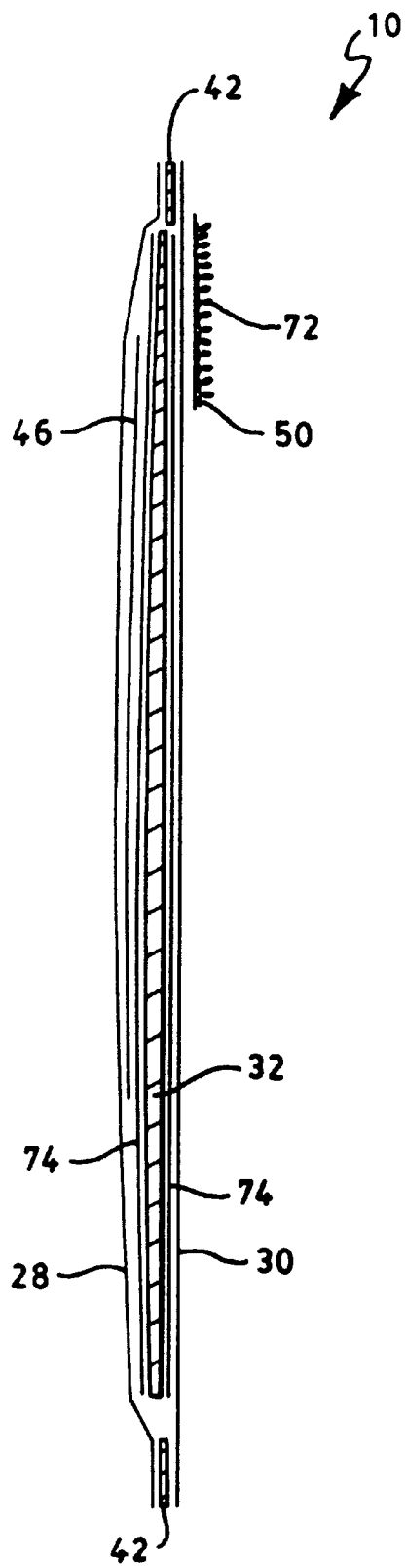
FIG. 3 representatively shows a schematic, longitudinal cross-sectional view of the article illustrated in FIG. 1.

With reference to FIGS. 1, 2 and 3, an article, such as diaper 10 has a lengthwise, longitudinal direction 26, a lateral cross-direction 24, a first article portion 12, a second article portion 14, and a fastener 36 for securing the first article portion 12 to the second article portion 14. The fastener 36 includes at least one first fastener component 70 attached to a lateral side section 86 of the first article portion 12, and a cooperating, second fastener component 72 attached to the second article portion 14. The first fastener component includes an engagement member substrate 56 having an appointed lift region 54, and a plurality of engagement members 40, such as the representatively shown prong-type hook members, which are operably attached to extend away from the engagement member substrate. The lift region 54 is disposed along at least a longitudinally extending, laterally outboard edge of the engagement substrate 56, and the lift region contains a plurality of engagement members which have been substantially deactivated.

In particular aspects of the invention, the engagement member substrate 56 can include an outboard, distal corner portion 92, and said lift region 54 is positioned at the outboard corner portion 92. In other aspects of the invention, the engagement member substrate 56 can include a laterally outboard, distal border portion 94, and the lift region 54 is located at a medial section of the outboard border portion 94.

The various aspects (individually and in combination) of the present invention can advantageously help to better maintain the desired fit around the wearer. For example, the aspects of the invention can help reduce the sagging and drooping of the crotch region of the garment, and can help reduce rollover and drooping at the waist region. The incorporation of the various aspects of the fastening system of the invention can provide improved securement with greater resistance to premature pop-opens, and can also help provide improved fit, greater comfort and reduced irritation of the wearer's skin. The distinctively configured combinations of engagement zones and finger lift tab regions can provide a distinctive cooperative arrangement of high engagement areas for greater securement and reliability, and predetermined areas of relatively lesser engagement for greater ease in the unfastening and removal of the article from a wearer. In particular, the distal or outboard end regions of the fastener tab can be more easily found and manipulated to initiate the desired unfastening operation.

The article of the invention can, for example, be a garment provided by the representatively shown disposable diaper 10. In desired aspects of the invention, the first article portion can provide a first, back waistband portion 12, and the second article portion can provide a second, front waistband portion 14. In addition, the article can have an intermediate or crotch portion 16 which interconnects between the first and second waistband portions 12 and 14, respectively. The diaper can further include a backsheet layer 30, a liquid permeable topsheet layer 28 connected and assembled in facing relation with the backsheet layer, and an absorbent structure, such as a structure which includes absorbent body 32. The absorbent structure is sandwiched between the backsheet and topsheet layers, and is operably held therebetween. A fastening system, such as the system including fasteners 36, is typically constructed and arranged to interconnect the first waistband portion 12 with the second waistband portion 14 to hold the article on a wearer. The fastening system can be operatively configured to join the first, back waistband portions 12 in an overlapping relation with the second, front waistband portion 14 in a back-to-front arrangement to thereby encircle the wearer's body and hold the diaper secure on the wearer during use. Optionally, the fastening system can employ fasteners 36 which are configured to join the front waistband portion 14 in an overlapping relation with the back waistband portions 12 in a front-to-back arrangement to secure the diaper. In such optional arrangement, the front waistband region may be identified as the first waistband portion 12 and the rear waistband region may be identified as the second waistband portion 14.

As representatively shown, the front waistband section 14 of the diaper 10 has a laterally opposed, front pair of side edge regions 88, and the rear waistband section 12 has a laterally opposed, rear pair of side edge regions 86. The intermediate section 16 interconnects the front and rear waistband section and provides a diaper crotch region which is typically positioned between the legs of the wearer. The article has an appointed fastener landing zone member 50 which is disposed on the outward surface of the article. In the configuration shown in FIGS. 1, 2 and 3, for example, the landing member 50 is disposed on the outward surface of the backsheet layer 30. The liquid permeable topsheet layer 28 is superposed in facing relation with the backsheet layer 30, and the absorbent body 32 is operably connected and affixed between the backsheet layer 30 and topsheet layer 28.

FIGS. 1 and 2 show typical plan views of the representative disposable diaper 10 in its generally flat-out, uncontracted state (i.e., with substantially all elastic induced gathering and contraction removed). In FIG. 1, the bodyside surface of the diaper which contacts the wearer is facing the viewer, and portions of the structure are partially cut away to more clearly show the interior construction of the diaper article. The outer edges of the diaper define a periphery with longitudinally extending side edge margins 20 and laterally extending end edge margins 22. The side edges define leg openings for the diaper, and optionally, are curvilinear and contoured. The end edges are shown as straight, but optionally, may be curvilinear.

With regard to the designated surfaces of the article, the various inward or bodyside surfaces are configured to face toward the body of the wearer when the article is placed about the wearer. The designated outward surfaces of the article is configured to face away from the wearer's body when the article is placed about the wearer.

The diaper 10 can typically include a porous, liquid permeable topsheet 28; a substantially liquid impermeable backsheet 30; an absorbent body structure 32 positioned and connected between the topsheet and backsheet; a surge management portion 46 located adjacent the absorbent structure; and a system of elastomeric gathering members, such as a system including leg elastics 34 and waist elastics 42. The surge management portion is posited in a liquid communication with an appointed storage or retention portion of the absorbent structure, and the topsheet 28, backsheet 30, absorbent structure 32, surge management portion 46 and elastic members 34 and 42 may be assembled together into a variety of well-known diaper configurations. The diaper can additionally include a system of containment flaps 62, and a system of side panel or ear region members 38, which may be elasticized or otherwise rendered elastomeric.

Examples of articles which include elasticized side panels and selectively configured fastener tabs are described in U.S. patent application Ser. No. 168,615 of T. Roessler et al., entitled DYNAMIC FITTING DIAPER, and filed Dec. 6, 1993 (attorney docket No. 10,961). Various techniques for forming the desired fastening systems are described in U.S. Pat. No. 5,399,219 of T. Roessler et al., entitled METHOD FOR MAKING A FASTENING SYSTEM FOR A DYNAMIC FITTING DIAPER which issued Mar. 21, 1995 (attorney docket No. 11,186); in U.S. patent application Ser. No. 286,086 of D. Fries, entitled A PROCESS FOR ASSEMBLING ELASTICIZED EAR PORTIONS and filed Aug. 3, 1994 (attorney docket No. 11,169) which corresponds to U.S. Pat. No. 5,540,796; and in U.S. patent application Ser. No. 08/415,383 of D. Fries, entitled AN ASSEMBLY PROCESS FOR A LAMINATED TAPE and filed Apr. 3, 1995 (attorney docket No. 11,950) which corresponds to U.S. Pat. No. 5,595,618. The disclosures of the above-described documents are incorporated herein by reference in a manner that is consistent (not in conflict) herewith.

The diaper 10 generally defines the longitudinally extending length direction 26 and the laterally extending width direction 24, as representatively shown in FIGS. 1 and 2. The diaper may have any desired shape, such as rectangular, I-shaped, a generally hourglass shape, or a T-shape. With the T-shape, the crossbar of the "T" may comprise the front waistband portion of the diaper, or may alternatively comprise the rear waistband portion of the diaper.

The topsheet 28 and backsheet 30 may be generally coextensive, and may have length and width dimensions which are generally larger than and extend beyond the corresponding dimensions of the absorbent structure 32 to provide for the corresponding side margins 20 and end margins 22. Optionally, the topsheet and backsheet layers may not be coextensive. The topsheet 28 is operatively associated with and superimposed on backsheet 30, thereby defining the periphery of the diaper. The waistband regions comprise those portions of the diaper, which when worn, wholly or partially cover or encircle the waist or mid-lower torso of the wearer. The intermediate, crotch region 16 lies between and interconnects the waistband regions 14 and 12, and comprises that portion of the diaper which, when worn, is positioned between the legs of the wearer and covers the lower torso of the wearer. Thus, the intermediate crotch region 16 is an area where repeated fluid surges typically occur in the diaper or other disposable absorbent article.

The backsheet 30 can typically be located along an outer-side surface of the absorbent body 32 and may be composed of a liquid permeable material, but desirably comprises a material which is configured to be substantially impermeable to liquids. For example, a typical backsheet can be manufactured from a thin plastic film, or other flexible, substantially liquid-impermeable material. As used in the present specification, the term "flexible" refers to materials which are compliant and which will readily conform to the general shape and contours of the wearer's body. The backsheet 30 prevents the exudates contained in absorbent body 32 from wetting articles, such as bedsheets and overgarments, which contact diaper 10. In particular embodiments of the invention, the backsheet 30 can include a film, such as a polyethylene film, having a thickness of from about 0.012 millimeters (0.5 mil) to about 0.051 millimeters (2.0 mils). For example, the backsheet film can have a thickness of about 1.25 mil.

Alternative constructions of the backsheet may comprise a woven or non-woven fibrous web layer which has been totally or partially constructed or treated to impart the desired levels of liquid impermeability to selected regions that are adjacent or proximate the absorbent body. For example, the backsheet may include a gas-permeable, non-woven fabric layer laminated to a polymer film layer which may or may not be gas-permeable. Other examples of fibrous, cloth-like backsheet materials can comprise a stretch thinned or stretch thermal laminate material composed of a 0.6 mil (0.015 mm) thick polypropylene blown film and a 0.7 ounce per square yard (23.8 gsm) polypropylene spunbond material (2 denier fibers). A material of this type forms the outercover of a HUGGIES SUPREME disposable diaper, which is commercially available from Kimberly-Clark Corporation. The backsheet 30 typically provides the outer cover of the article. Optionally, however, the article may include a separate outer cover component member which is additional to the backsheet.

The backsheet 30 may alternatively include a microporous, "breathable" material which permits gases, such as water vapor, to escape from the absorbent body 32 while substantially preventing liquid exudates from passing through the backsheet. For example, the breathable backsheet may be composed of a microporous polymer film or a nonwoven fabric which has been coated or otherwise modified to impart a desired level of liquid impermeability. For example, a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn. The backsheet may also be embossed or otherwise provided with a pattern or matte finish to exhibit a more aesthetically pleasing appearance.

In the various configurations of the invention, where a component such as the backsheet 30 or the containment flaps 62 are configured to be permeable to gas while having a resistance and limited permeability to aqueous liquid, the liquid resistant material can have a construction which is capable of supporting a hydrohead of at least about 45 cm of water substantially without leakage therethrough. A suitable technique for determining the resistance of a material to liquid penetration is Federal Test Method Standard FTMS 191 Method 5514, 1978, or an equivalent thereof.

The size of the backsheet 30 is typically determined by the size of absorbent body 32 and the particular diaper design selected. Backsheet 30, for example, may have a generally T-shape, a generally I-shape or a modified hourglass shape, and may extend beyond the terminal edges of absorbent body 32 by a selected distance, such as a distance within the range of about 1.3 centimeters to 2.5 centimeters (about 0.5 to 1 inch), to provide at least a portion of the side and end margins.

The topsheet 28 presents a body-facing surface which is compliant, soft-feeling, and non-irritating to the wearer's skin. Further, the topsheet 28 can be less hydrophilic than absorbent body 32, and is sufficiently porous to be liquid permeable, permitting liquid to readily penetrate through its thickness to reach the absorbent body. A suitable topsheet layer 28 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The topsheet layer 28 is typically employed to help isolate the wearer's skin from liquids held in absorbent body 32.

Various woven and nonwoven fabrics can be used for topsheet 28. For example, the topsheet may be composed of a meltblown or spunbonded web of the desired fibers, and may also be a bonded-carded-web. The various fabrics can be composed of natural fibers, synthetic fibers or combinations thereof.

For the purposes of the present description, the term "nonwoven web" means a web of fibrous material which is formed without the aid of a textile weaving or knitting process. The term "fabrics" is used to refer to all of the woven, knitted and nonwoven fibrous webs.

The topsheet fabrics may be composed of a substantially hydrophobic material, and the hydrophobic material may optionally be treated with a surfactant or otherwise processed to impart a desired level of wettability and hydrophilicity. In a particular embodiment of the invention, topsheet 28 is a nonwoven, spunbond polypropylene fabric composed of about 2.8–3.2 denier fibers formed into a web having a basis weight of about 22 gsm and density of about 0.06 gm/cc. The fabric can be surface treated with an operative amount of surfactant, such as about 0.28% TRITON X-102 surfactant. The surfactant can be applied by any conventional means, such as spraying, printing, brush coating or the like.

The topsheet 28 and backsheet 30 are connected or otherwise associated together in an operable manner. As used herein, the term "associated" encompasses configurations in which topsheet 28 is directly joined to backsheet 30 by affixing topsheet 28 directly to backsheet 30, and configurations wherein topsheet 28 is indirectly joined to backsheet 30 by affixing topsheet 28 to intermediate members which in turn are affixed to backsheet 30. Topsheet 28 and backsheet 30 can, for example, be joined to each other in at least a portion of the diaper periphery by suitable attachment mechanisms (not shown) such as adhesive bonds, sonic bonds, thermal bonds, pinning, stitching or any other attachment technique known in the art, as well as combinations thereof. For example, a uniform continuous layer of adhesive, a patterned layer of adhesive, a sprayed pattern of adhesive or an array of separate lines, swirls or spots of construction adhesive may be used to affix the topsheet 28 to the backsheet 30. It should be readily appreciated that the above-described attachment means may also be employed to suitably interconnect, assemble and/or affix together the various other component parts of the articles which are described herein.

The absorbent body 32 provides an absorbent structure which can include a retention portion, such as the shown absorbent pad composed of selected hydrophilic fibers and high-absorbency particles, which holds and stores absorbed liquids and other waste materials. The absorbent body is positioned and sandwiched between the topsheet 28 and backsheet 30 to form the diaper 10. The absorbent body has a construction which is generally compressible, conformable, non-irritating to the wearer's skin, and capable of absorbing and retaining body exudates. It should be understood that, for purposes of this invention, the absorbent body structure may comprise a single, integral piece of material, or alternatively, may comprise a plurality of individual separate pieces of material which are operably assembled together.

Various types of wettable, hydrophilic fibrous material can be used to form the component parts of absorbent body 32. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with such system, fibers having contact angles less than 90° are designated "wettable", while fibers having contact angles greater than 90° are designated "nonwettable".

The absorbent body structure 32 can comprise a matrix of hydrophilic fibers, such as a web of cellulosic fluff, mixed with particles of high-absorbency material. In particular arrangements, absorbent body 32 may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be nonuniformly mixed. For example, the concentrations of superabsorbent particles may be arranged in a non-step-wise gradient through a substantial portion of the thickness (z-direction) of the absorbent structure, with lower concentrations toward the bodyside of the absorbent body and relatively higher concentrations toward the outerside of the absorbent structure. Suitable z-gradient configurations are described in U.S. Pat. No. 4,699,823 issued Oct. 13, 1987 to Kellenberger et al., the entire disclosure of which is incorporated herein by reference in a manner that is consistent (not in conflict) with the present description. Alternatively, the concentrations of superabsorbent particles may be arranged in a non-step-wise gradient, through a substantial portion of the thickness (z-direction) of the absorbent structure, with higher concentrations toward the bodyside of the absorbent body and relatively lower concentrations toward the outerside of the absorbent structure. The superabsorbent particles may also be arranged in a generally discrete layer within the matrix of hydrophilic fibers. In addition, two or more different types of superabsorbent may be selectively positioned at different locations within or along the fiber matrix.

The high-absorbency material may comprise absorbent gelling materials, such as superabsorbents. Absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly (acrylic acid) and poly (methacrylic acid), poly (acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent body include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Synthetic absorbent gelling materials typically are xerogels which form hydrogels when wetted. The term "hydrogel", however, has commonly been used to also refer to both the wetted and unwetted forms of the material.

As mentioned previously, the high-absorbency material used in absorbent body 32 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in absorbent body 32. Desired for use are particles having an average size of from about 20 microns to about 1 millimeter. "Particle size" as used herein means the weighted average of the smallest dimension of the individual particles.

The hydrophilic fibers and high-absorbency particles can be configured to form an average composite basis weight which is within the range of about 400–900 gsm. In certain aspects of the invention, the average composite basis weight is within the range of about 500–800 gsm, and alternatively is within the range of about 550–750 gsm to provide desired performance.

To improve the containment of the high-absorbency material, absorbent body structure 32 can include an overwrap, such as wrap sheet 74, which is placed immediately adjacent and around absorbent body 32 and may be bonded to the absorbent structure and to the various other components of the article. The wrap sheet is preferably a layer of absorbent material which covers the major bodyside and outerside surfaces of the absorbent body, and preferably encloses substantially all of the peripheral edges of the absorbent body to form a substantially complete envelope thereabout. Alternatively, the wrap sheet can provide an absorbent wrapping which covers the major bodyside and outerside surfaces of the absorbent body, and encloses substantially only the lateral side edges of the absorbent body. Accordingly, both the linear and the inwardly curved portions of the lateral side edges of the wrap sheet would be closed about the absorbent body. In such an arrangement, however, the end edges of the wrap sheet may not be completely closed around the end edges of the absorbent body at the waistband regions of the article.

For example, the complete wrap sheet 74, or at least the bodyside layer of the wrap sheet, may comprise a meltblown web composed of meltblown fibers, such as meltblown polypropylene fibers. Another example of absorbent wrap 74 may comprise a low porosity cellulosic web, such as a tissue composed of an approximately 50/50 blend of hardwood/softwood fibers.

The absorbent wrap 74 may comprise a multi-element wrapsheet which includes a separate bodyside wrap layer and a separate outerside wrap layer, each of which extends past all or some of the peripheral edges of absorbent body 32. Such a configuration of the wrap sheet can, for example, facilitate the formation of a substantially complete sealing and closure around the peripheral edges of absorbent body 32. In the back waistband portion of the illustrated diaper, the absorbent wrap may also be configured to extend an increased distance away from the periphery of the absorbent body to add opacity and strength to the back side-sections of the diaper. In the illustrated embodiment, the bodyside and outerside layers of absorbent wrap 74 can extend at least about ½ inch beyond the peripheral edges of the absorbent body to provide an outwardly protruding, flange-type bonding area over which the periphery of the bodyside portion of the absorbent wrap may be completely or partially connected to the periphery of the outerside portion of the absorbent wrap.

The bodyside and outerside layers of wrap sheet 74 may be composed of substantially the same material, or may be composed of different materials. For example, the outerside layer of the wrap sheet may be composed of a relatively lower basis weight material having a relatively high porosity, such as a wet strength cellulosic tissue composed of softwood pulp. The bodyside layer of the wrap sheet may comprise one of the previously described wrap sheet materials which has a relatively low porosity. The low porosity bodyside layer can better prevent the migration of superabsorbent particles onto the wearer's skin, and the high porosity, lower basis weight outerside layer can help reduce costs.

Diaper 10 can also include a surge management layer 46 which helps to decelerate and diffuse surges or gushes of liquid that may be rapidly introduced into the absorbent body of the article. Desirably, the surge management layer can rapidly accept and temporarily hold the liquid prior to releasing the liquid into the storage or retention portions of the absorbent structure. In the illustrated embodiment, for example, surge layer 46 can be located on an inwardly facing body side surface of topsheet layer 28. Alternatively, surge layer 46 may be located adjacent to an outer side surface of topsheet 28. Accordingly, the surge layer would then be interposed between topsheet 28 and absorbent body 32. Examples of suitable surge management layers 46 are described in U.S. patent application Serial No. 206,986 of C. Ellis and D. Bishop, entitled FIBROUS NONWOVEN WEB SURGE LAYER FOR PERSONAL CARE ABSORBENT ARTICLES AND THE LIKE, filed Mar. 4, 1994 (attorney docket No. 11,256) which corresponds to U.S. Pat. No. 5,486,166; and U.S. patent application Ser. No. 206,069 of C. Ellis and R. Everett, entitled IMPROVED SURGE MANAGEMENT FIBROUS NONWOVEN WEB FOR PERSONAL CARE ABSORBENT ARTICLES AND THE LIKE, filed Mar. 4, 1994 (attorney docket No. 11,387) which corresponds to U.S. Pat. No. 5,490,846; the entire disclosures of which are hereby incorporated by reference in a manner that is consistent herewith.

The leg elastic members 34 are located in the lateral side margins 20 of diaper 10, and are arranged to draw and hold diaper 10 against the legs of the wearer. The elastic members are secured to diaper 10 in an elastically contractible condition so that in a normal under strain configuration, the elastic members effectively contract against diaper 10. The elastic members can be secured in an elastically contractible condition in at least two ways, for example, the elastic members may be stretched and secured while diaper 10 is in an uncontracted condition. Alternatively, diaper 10 may be contracted, for example, by pleating, and the elastic members secured and connected to diaper 10 while the elastic members are in their relaxed or unstretched condition. Still other mechanisms, such as heat-shrink elastic material, may be used to gather the garment.

In the embodiment illustrated in FIGS. 1 and 2, the leg elastic members 34 extend essentially along the complete length of the intermediate crotch region 16 of diaper 10. Alternatively, elastic members 34 may extend the entire length of diaper 10, or any other length suitable for providing the arrangement of elastically contractible lines desired for the particular diaper design.

The elastic members 34 may have any of a multitude of configurations. For example, the width of the individual elastic members 34 may be varied from about 0.25 millimeters (0.01 inch) to about 25 millimeters (1.0 inch) or more. The elastic members may comprise a single strand of elastic material, or may comprise several parallel or non-parallel strands of elastic material, or may be applied in a rectilinear or curvilinear arrangement. Where the strands are non-parallel, two or more of the strands may intersect or otherwise interconnect within the elastic member. The elastic members may be affixed to the diaper in any of several ways which are known in the art. For example, the elastic members may be ultrasonically bonded, heat and pressure sealed using a variety of bonding patterns, or adhesively bonded to diaper 10 with sprayed or swirled patterns of hotmelt adhesive.

In particular embodiments of the invention, the leg elastic members 34 may include a carrier sheet to which are attached a grouped set of elastics composed of a plurality of individual elastic strands. The elastic strands may intersect or be interconnected, or be entirely separated from each other. The carrier sheet may, for example, comprise a 0.002 cm thick polymer film, such as a film of unembossed polypropylene material. The elastic strands can, for example, be composed of LYCRA elastomer available from DuPont, a business having offices in Wilmington, Del. Each elastic strand is typically within the range of about 470–1500 decitex (dtx), and may be about 940–1050 dtx. In particular embodiments of the invention, for example, three or four strands can be employed for each elasticized legband.

In addition, the leg elastics 34 may be generally straight or optionally curved. For example, the curved elastics can be inwardly bowed toward the longitudinal centerline of the diaper. In particular arrangements, the curvature of the elastics may not be configured or positioned symmetrically relative to the lateral centerline of the diaper. The curved elastics may have an inwardly bowed and outwardly bowed, reflex-type of curvature, and the length-wise center of the elastics may optionally be offset by a selected distance toward either the front or rear waistband of the diaper to provide desired fit and appearance. In particular embodiments of the invention, the innermost point (apex) of the set of curved elastics can be offset towards the front or rear waistband of the diaper, and the outwardly bowed reflexed-portion can be positioned toward the diaper front waistband.

As representatively shown, the diaper 10 can include a waist elastic 42 positioned in the longitudinal margins of either or both of the front waistband 14 and the rear waistband 12. The waist elastics may be composed of any suitable elastomeric material, such as an elastomer film, an elastic foam, multiple elastic strands, an elastomeric fabric or the like. For example, suitable elastic waist constructions are described in U.S. Pat. No. 4,916,005 to Lippert et al., the entire disclosure of which is hereby incorporated by reference in a manner that is consistent herewith.

With reference to the representative configurations shown in FIGS. 1 and 2, the article can include a system of "ear" regions or ear members 38. In particular arrangements, each ear region or member 38 extends laterally at the opposed, lateral ends of at least one waistband portion of backsheet 30, such as the representatively shown rear waistband portion 12, to provide terminal side sections of the article. In addition, each ear region can substantially span from a laterally extending, terminal waistband edge to approximately the location of its associated and corresponding leg opening section of the diaper. The diaper 10, for example, has a laterally opposed pair of leg openings provided by the curved margins of the ear regions in combination with the correspondingly adjacent, medial sections of the shown pair of longitudinally extending, side edge regions 20 (FIG. 1).

In the various configurations of the invention, the ear regions may be integrally formed with a selected diaper component. For example, ear regions 38 can be integrally formed from the layer of material which provides backsheet layer 30, or may be integrally formed from the material employed to provide topsheet 28. In alternative configurations, the ear regions 38 may be provided by one or more separately provided members that are connected and assembled to the backsheet 30, to the topsheet 28, in between the backsheet and topsheet, or in various fixedly attached combinations of such assemblies.

In particular configurations of the invention, each of the ear regions 38 may be formed from a separately provided piece of material which is then suitably assembled and attached to the selected front and/or rear waistband portion of the diaper article. For example, each ear region 38 may be attached to the rear waistband portion of the backsheet 30 along a ear region attachment zone, and can be operably attached to either or both of the backsheet and topsheet components of the article. The inboard, attachment zone region of each ear region can be overlapped and laminated with its corresponding, lateral end edge region of the waistband section of the article. The ear regions extend laterally to form a pair of opposed waist-flap sections of the diaper, and are attached with suitable connecting means, such as adhesive bonding, thermal bonding, ultrasonic bonding, clips, staples, sewing or the like. Desirably, the ear regions extend laterally beyond the terminal side edges of the backsheet layer and topsheet layer at the corresponding, attached waistband section of the article.

The ear regions 38 may be composed of a substantially non-elastomeric material, such as polymer films, woven fabrics, nonwoven fabrics or the like, as well as combinations thereof. In particular aspects of the invention, ear regions 38 may be composed of a substantially elastomeric material, such as a stretch-bonded-laminate (SBL) material, a neck-bonded-laminate (NBL) material, an elastomeric film, an elastomeric foam material, or the like, which is elastomerically stretchable at least along the lateral direction 24. For example, suitable meltblown elastomeric fibrous webs for forming ear regions 38 are described in U.S. Pat. No. 4,663,220 issued May 5, 1987 to T. Wisneski et al., the entire disclosure of which is hereby incorporated by reference. Examples of composite fabrics comprising at least one layer of nonwoven textile fabric secured to a fibrous elastic layer are described in European Patent Application EP 0 217 032 A2 published on Apr. 8, 1987 which has the listed inventors of J. Taylor et al., the entire disclosure of which is hereby incorporated by reference. Examples of NBL materials are described in U.S. Pat. No. 5,226,992 issued Jul. 13, 1993 to Mormon, the entire disclosure of which is hereby incorporated by reference.

As previously mentioned, various suitable constructions can be employed to attach the ear regions 38 to the selected waistband portions of the article. Particular examples of suitable constructions for securing a pair of elastically stretchable members to the lateral, side portions of an article to extend laterally outward beyond the laterally opposed side regions of the outer cover and liner components of an article can be found in U.S. Pat. No. 4,938,753 issued Jul. 3, 1990 to P. VanGompel et al., the entire disclosure of which is hereby incorporated by reference in a manner that is consistent herewith.

Each of the ear regions 38 extends laterally at a one of the opposed lateral ends of at least one waistband section of the diaper 10. In the shown embodiment, for example, a first pair of ear regions extend laterally at the opposed lateral ends of the back waistband section of the backsheet 30, and a second pair of ear regions extend laterally at the opposed lateral ends of the front waistband section of the backsheet. The illustrated ear regions have a tapered, curved or otherwise contoured shape in which the longitudinal length of the relatively inboard base region is larger or smaller than the longitudinal length of its relatively outboard end region. Alternatively, the ear regions may have a substantially rectangular shape, and optionally may have a substantially trapezoidal shape.

Diaper 10 can also include a pair of elasticized containment flaps 62 which extend generally length-wise along the longitudinal direction 26 of the diaper. The containment flaps are typically positioned laterally inboard from leg elastics 34, and substantially symmetrically placed on each side of the lengthwise, longitudinal centerline of the diaper. In the illustrated arrangements, each containment flap 62 has a substantially fixed edge portion 64 and a substantially moveable edge portion 66, and is operably elasticized to help each containment flap to closely contact and conform to the contours of the wearer's body. Examples of suitable containment flap constructions are described in U.S. Pat. No. 4,704,116 issued Nov. 3, 1987, to K. Enloe, the entire disclosure of which is hereby incorporated by reference in a manner that is consistent herewith. The containment flaps may be composed of a wettable or a non-wettable material, as desired. In addition, the containment flap material may be substantially liquid-impermeable, may be permeable to only gas or may be permeable to both gas and liquid. Other suitable containment flap configurations are described in U.S. patent application Ser. No. 206,816 of R. Everett et al., filed Mar. 4, 1994 and entitled ABSORBENT ARTICLE HAVING AN IMPROVED SURGE MANAGEMENT (attorney docket No. 11,375), which corresponds to U.S. Pat. No. 5,562,650, the disclosure of which is hereby incorporated by reference in a manner that is consistent herewith.

In optional, alternative configurations of the invention, diaper 10 may include internal, elasticized, containment waist flaps, such as those described in U.S. Pat. No. 4,753,646 issued Jun. 28, 1988, to K. Enloe, and in U.S. patent application Ser. No. 560,525 of D. Laux et al. entitled AN ABSORBENT ARTICLE WITH IMPROVED ELASTIC MARGINS AND CONTAINMENT SYSTEM and filed Dec. 18, 1995 (attorney docket No. 11,091), the entire disclosures of which are hereby incorporated by reference in a manner that is consistent herewith. Similar to the construction of the containment flaps, the containment waist flaps may be composed of a wettable or non-wettable material, as desired. The waist flap material may be substantially liquid-impermeable, permeable to only gas, or permeable to both gas and liquid.

To provide a desired refastenable fastening system, diaper 10 can include one or more, appointed landing member regions or patches, such as provided by the representatively shown, primary landing member 50. The landing member can provide an operable target area for generating a releasable and re-attachable securement with at least one of the fastener tabs 36. In desired embodiments of the invention, the landing member patch can be positioned on the front waistband portion 14 of the diaper and located on the outward surface of the backsheet layer 30. Alternatively, the landing member patch can be positioned on an appointed inward surface of the diaper, such as the bodyside surface of the topsheet layer 28.

Particular arrangements of the invention can include one or more landing members 50 which can be directly or indirectly attached to the second waistband portion 14. Desirably, the landing members are affixed directly to the outward surface of the appropriate waistband portion, but may optionally be joined to the inward, bodyside surface of the article waistband portion.

In the various configurations of the invention, the landing member 50 can be composed of a substantially non-elastomeric material, such as polymer films or tapes, woven fabrics, nonwoven fabrics or the like, as well as combinations thereof. In particular configurations of the invention, the landing member may be composed of a substantially elastomeric material, such as a stretch-bonded-laminate (SBL) material, a neck-bonded-laminate (NBL) material, an elastomeric film, an elastomeric foam material, or the like, which is elastomerically stretchable at least along the lateral direction 24.

The various configurations of the invention can include at least one separately provided fastener tab 36 located at either or both of the lateral end regions 86 of the back waistband 12. Alternatively, at least one fastener tab 36 can be located at either or both of the lateral end regions 88 of the front waistband 14. The representatively shown embodiment, for example, has a laterally opposed pair of the fastener tabs 36 with a one of the fastener tabs located at each of the distal side edges of the rear waistband 12. More particularly, each of the fasteners 36 is assembled and attached to project and extend from a corresponding, immediately adjacent ear region located at one of the opposed, lateral end regions 86 of the front waistband section 12.

The fastener tab 36 can be composed of a substantially non-elastomeric material, such as polymer films or tapes, woven fabrics, nonwoven fabrics or the like, as well as combinations thereof. Optionally, the fastener tab may be composed of a substantially elastomeric material, such as a stretch-bonded-laminate (SBL) material, a neck-bonded-laminate (NBL) material, an elastomeric film, an elastomeric foam material, or the like, which is elastomerically stretchable at least along the lateral direction 24.

In the various aspects and configurations of the invention, the fastening mechanism between the selected first fastener component and the selected, second fastener component may be adhesive, cohesive, mechanical or combinations thereof. In the context of the present invention, a mechanical fastening system is a system which includes cooperating, first and second components which mechanically inter-engage to provide a desired securement.

Desirably, the first and second fastener components include complementary elements of a cooperatively interengaging mechanical fastening system. The mechanical fastener components can be provided by mechanical-type fasteners such as hooks, buckles, snaps, buttons and the like, which include cooperating and complementary, mechanically interlocking components.

As shown in the illustrated arrangements, for example, the mechanical fastening system may be a hook-and-loop type of fastening system. Such fastening systems generally comprise a "hook" or hook-like, male component, and a cooperating "loop" or loop-like, female component which engages and releasably interconnects with the hook component. Desirably, the interconnection is selectively releasable and re-attachable. Conventional systems are, for example, available under the VELCRO trademark. The hook element may be provided by a single-prong hook configuration, a multiple-prong hook configuration or by a generally continuous, expanded-head configuration, such as provided by a mushroom-head type of hook element. The loop element may be provided by a woven fabric, a nonwoven fabric, a knitted fabric, a perforated or apertured layer, and the like, as well as combinations thereof. The many arrangements and variations of such fastener systems have been collectively referred to as hook-and-loop fasteners.

A configuration which employs a selectively releasable, interengaging mechanical fastening system can, for example, locate the first fastener component on at least the appointed mating or securing surface of the fastener tab 36, and can locate the cooperating, second fastener component on the appointed engagement surface of the appointed landing member 50. For example, with the representatively shown hook-and-loop fastener, the fastening component which is attached to the appointed mating or securing surface of the fastener tab 36 may include a hook type of mechanical fastening element, and the complementary fastening component, which is operably joined and attached to the appointed landing zone member 50 can include a loop type of fastening element.

It should also be readily apparent that, in the various configurations of the invention, the relative positions and/or materials of the first fastening component and its cooperating, complementary second fastening component can be transposed. Accordingly, the fastening component, which is attached to the appointed mating surface of the fastener tabs 36, may include a loop type of mechanical fastening element; and the complementary, second fastening component, which is operatively joined and attached to the appointed landing zone member, can include a hook type of fastening element.

Examples of hook-and-loop fastening systems and components are described in U.S. Pat. No. 5,019,073 issued May 28, 1991 to T. Roessler et al., the entire disclosure of which is hereby incorporated by reference in a manner that is consistent herewith. Other examples of hook-and-loop fastening systems are described in U.S. patent application Ser. No. 366,080 entitled HIGH-PEEL TAB FASTENER, filed Dec. 28, 1994 by G. Zehner et al. (attorney docket No. 11,571) which corresponds to U.S. Pat. No. 5,605,735; and U.S. patent application Ser. No. 421,640 entitled MULTI-ATTACHMENT FASTENING SYSTEM, filed Apr. 13, 1995 by P. VanGompel et al.; the entire disclosures of which are hereby incorporated by reference in a manner that is consistent herewith. Examples of fastening tabs constructed with a carrier layer are described in U.S. patent application Ser. No. 08/603,477 of A. Long et al., entitled MECHANICAL FASTENING SYSTEM WITH GRIP TAB and filed Mar. 6, 1996 (attorney docket No. 12,563) which corresponds to U.S. Pat. No. 5,624,429 which issued Apr. 29, 1997, the entire disclosure of which is hereby incorporated by reference in a manner which is consistent herewith.

Each fastener tab 36 can have a variety of rectilinear or curvilinear shapes and planforms, as well as combinations thereof. For example, as illustrated in the representatively shown arrangements, the fastener tab can have a quadrilateral, generally rectangular shape. In addition, the longitudinally extending, laterally outward, terminal edge of the fastener tab may be substantially straight, as representatively shown in FIGS. 4 through 4B. Alternatively, the longitudinally extending, laterally outward, terminal edge of the fastener tab may have only a limited amount of waviness, as representatively shown in FIGS. 5 and 6.

The first fastener component includes the engagement member substrate 56 having the appointed lift region 54. As representatively shown in FIGS. 5 through 6B, the engagement substrate 56 can be disposed along at least a portion of a longitudinally extending, laterally outboard edge of the fastener tab 36, and can be constructed to be substantially coterminous with the fastener tab, particularly with respect to the laterally outward edge of the fastener tab. Additionally, the engagement substrate 56 can be disposed along at least a portion of at least one laterally extending, longitudinally outward edge of the fastener tab 36, and can be configured to be substantially coterminous with the fastener tab, particularly with respect to the longitudinally outward edges of the fastener tab.

The appointed lift region 54 can also be disposed along at least a portion of a longitudinally extending, laterally outboard edge of the engagement substrate 56, and can be constructed to be substantially coterminous with the engagement substrate, particularly with respect to the laterally outward edges of the engagement substrate. Additionally, the lift region 54 can be disposed along at least a portion of at least one laterally extending, longitudinally outward, terminal edge of the engagement substrate 56, and can be configured to be substantially coterminous with the engagement substrate, particularly with respect to the longitudinally outward, terminal edges of the engagement substrate.

The appointed lift region 54 can further be disposed along at least a portion of a longitudinally extending, laterally outboard edge of the fastener tab 36, and can be constructed to be substantially coterminous with the fastener tab, particularly with respect to the laterally outward, terminal edge of the fastener tab. Additionally, the lift region 54 can be disposed along at least a portion of at least one laterally extending, longitudinally outward, terminal edge of the fastener tab 36, and can be configured to be substantially coterminous with the fastener tab, particularly with respect to the longitudinally outward edges of the fastener tab.

A plurality of engagement members 40, such as the representatively shown prong-type hook members, are operably attached to extend away from the engagement substrate 56 and are configured to provide an operative fastening engagement with the appointed second mechanical fastener component 72. The engagement members are arranged in an operative distribution and an operative concentration, and a substantially continuous presence of the engagement members can be arranged to extend to the longitudinally extending, laterally outward edge or edges of the engagement substrate 56. Additionally, the substantially continuous presence of the engagement members can be arranged to extend to the longitudinally extending, laterally outward edge or edges of the fastener tab 36.

The substantially continuous presence of the engagement members can also be arranged to extend to either of the laterally extending, longitudinally outward edges of the engagement substrate 56. Desirably, the presence of the engagement members can be arranged to extend to both of the longitudinally outward edges of their corresponding engagement substrate. Additionally, the substantially continuous presence of the engagement members can also be arranged to extend to either of the laterally extending, longitudinally outward edges of the fastener tab 36. Desirably, the presence of at least a portion of the engagement members can be arranged to extend to both of the longitudinally outward edges of their corresponding fastener tab.

The engagement members 40 have previously been present in their operative configuration in the lift region 54 of the first mechanical fastener component 70, but at least an operably sufficient portion of the engagement members in the lift region have been subsequently treated to become substantially non-engaging with the appointed, second mechanical fastener component 72. Accordingly, a plurality of the engagement members in the lift region 54 have been substantially deactivated to provide an area region of substantially inoperative engagement members 41.

Figure 7:
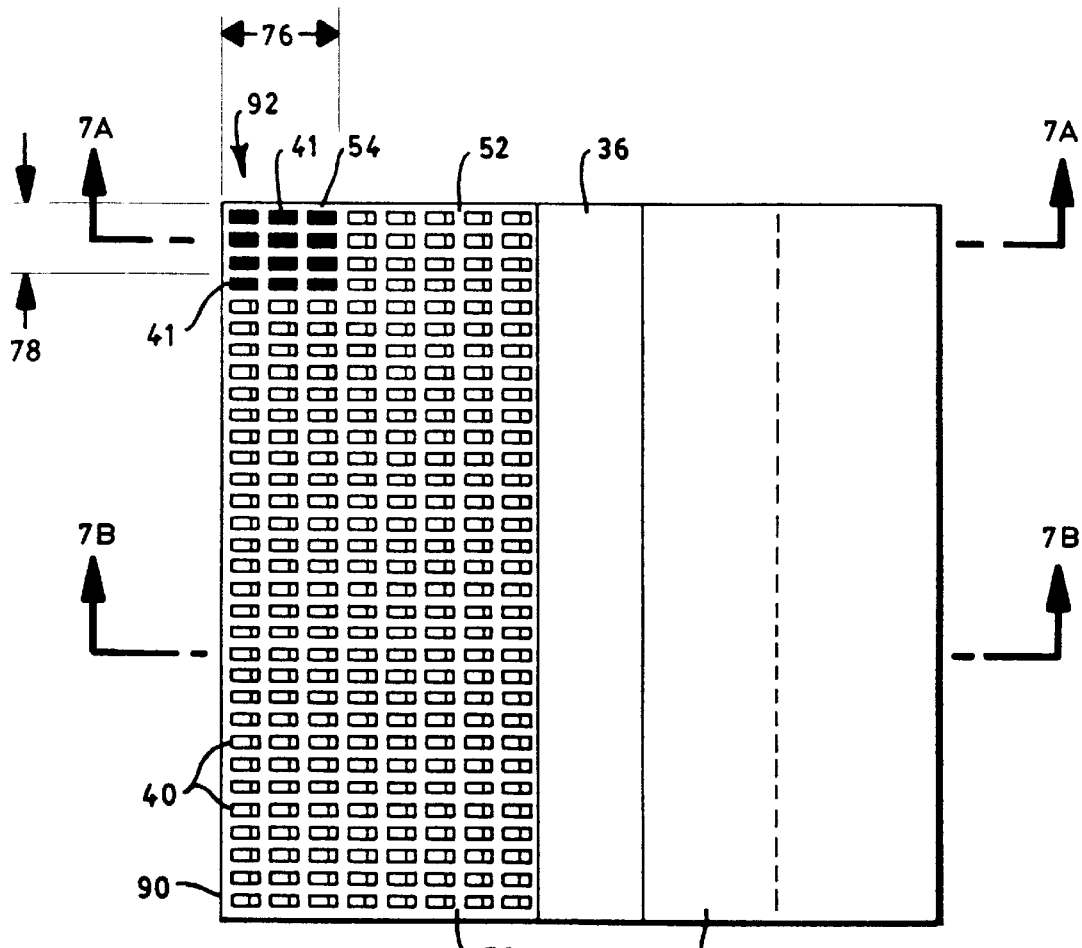
FIG. 7 representatively shows a top view of an assembly of the side panel joined with another fastening tab of the invention having a rectangular corner lift region.
Figure 7A:
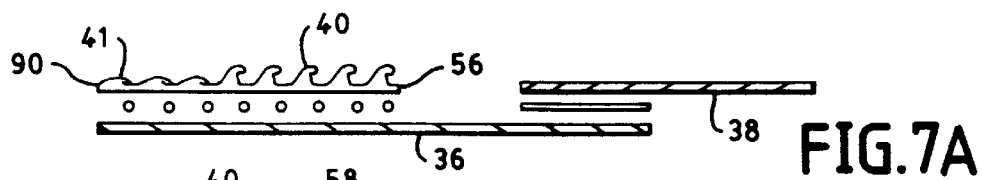
FIG. 7A representatively shows a schematic, laterally extending, expanded edge view along line 7A—7A of the fastening tab assembly illustrated in FIG. 7.
Figure 7B:
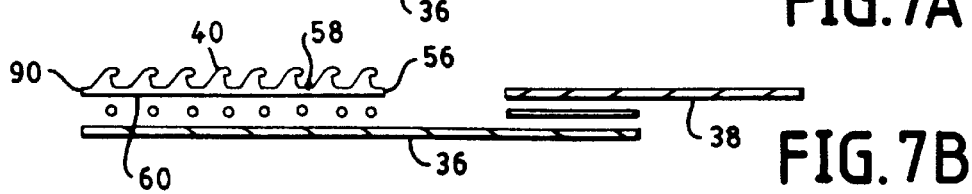
FIG. 7B representatively shows a schematic, laterally extending, expanded edge view along line 7B—7B of the fastening tab assembly illustrated in FIG. 7.

With reference to FIGS. 4 through 4B, the first mechanical fastener component 70 can include an outboard, distally terminal corner portion 92, and the lift region 54 can be positioned at the outboard corner portion of the first fastener component. In the representatively shown arrangement, for example, the engagement member substrate 56 can provide the corner portion 92, and the lift region 54 can be positioned at the outboard, terminal corner portion of the substrate material. As illustrated, the lift region 54 can be generally triangular in shape. Optionally, the shape of the corner lift region 54 can be generally rectangular (FIG. 7) or other polygonal-shaped, elliptical or semi-elliptical shaped, circular or semi-circular shaped, pie-shaped, crescent-shaped (FIG. 8), or the like, as well as combinations thereof.

The operative engagement members 40 in the primary engagement section 52 are present immediately adjacent to a perimeter of the appointed lift region 54, and are desirably arranged to form a substantially continuous and substantially contiguous mass of engagement members. The substantially contiguous mass of engagement members extends along the portions of the lift region perimeter which lie within the area of the engagement substrate 56 and which do not correspond to the outward, terminal edges of the engagement substrate. Thus, the contiguous mass of engagement members can extend substantially continuously along the perimeter edges of the lift region which are inboard from the terminal edges of the substrate 56. The substantially contiguous mass of engagement members can continuously bracket and partially surround the area of the lift region 54.

With reference to FIGS. 9 through 9B, the first fastener component 70 can include a laterally outboard, distal border portion 94, and the lift region 54 can be located at and restricted to an appointed medial section of the outboard border portion 94 to provide an indented-type lift region. In particular arrangements, the engagement member substrate 56 of the first fastener component can be disposed along the laterally outboard, distal border portion 94. Additionally, the lift region 54 can be located at an appointed medial section of the outboard border portion of the engagement member substrate 56. As a result, a longitudinally opposed pair of extending arm sections 80 of the primary engagement section 52 can be configured to project laterally and bracket the longitudinally opposed, end-sections of the lift region 54. Thus, the lift region 54 can have the configuration of a pocket or indentation which extends into the area of the fastener tab 36. As illustrated in the representatively shown arrangement, the indented-type lift region can also have the form of an indented area which extends into and across an appointed portion of the area of the engagement member substrate layer 56. Accordingly, the outline shape of an inboard perimeter edge of the indented lift region is substantially concave in the laterally outward direction. The indented lift region 54 can, for example, be generally triangular, rectangular or other polygonal-shaped, elliptical or semi-elliptical shaped, circular or semicircular shaped, pie-shaped, crescent-shaped, or the like, as well as combinations thereof.

Again, the operative engagement members 40 in the primary engagement section 52 are present immediately adjacent to a perimeter of the indented lift region 54, and are desirably arranged to form a substantially continuous and substantially contiguous mass of engagement members. Such contiguous mass of engagement members extends substantially continuously along the portions of the lift region perimeter which lie within the area of the engagement substrate 56 and do not correspond to the outward, terminal edges of the engagement substrate. Thus, the contiguous mass of engagement members can extend substantially continuously along the inboard perimeter edges of the lift region.

In the various configurations of the invention, the substantially contiguous mass of engagement members can extend along at least a minimum of about 30% of a total perimeter of the appointed lift region 54. Alternatively, the substantially contiguous mass of engagement members extend along at least about 35% of the total perimeter of the appointed lift region, and optionally, can extend along at least about 40% of the total perimeter of the appointed lift region to provide improved performance. In other aspects, the substantially contiguous mass of engagement members extend along a maximum of not more than about 80% of the total perimeter of the appointed lift region 54. Alternatively, the substantially contiguous mass of engagement members extend along not more than about 75% of the total perimeter of the appointed lift region, and optionally, extend along not more than about 70% of the total perimeter of the appointed lift region to provide improved performance. With the corner-type lift region 54, the substantially contiguous mass of engagement members are more likely to extend along the perimeter of the lift region in percentages of the total perimeter which include the lower end of the described ranges. With indented-type lift region, the substantially contiguous mass of engagement members are more likely to extend along the perimeter of the lift region in percentages of the total perimeter which include the upper end of the described ranges.

In particular aspects of the corner-type lift region 54, the substantially contiguous mass of engagement members can extend along at least a minimum of about 30% of a total perimeter of the appointed lift region 54. Alternatively, the substantially contiguous mass of engagement members extend along at least about 35% of the total perimeter of the appointed lift region, and optionally, can extend along at least about 40% of the total perimeter of the appointed lift region to provide improved performance. In other aspects, the substantially contiguous mass of engagement members extend along a maximum of not more than about 60% of the total perimeter of the appointed lift region 54. Alternatively, the substantially contiguous mass of engagement members extend along not more than about 50% of the total perimeter of the appointed lift region, and optionally, extend along not more than about 45% of the total perimeter of the appointed lift region to provide improved performance.

In particular aspects of the indented-type lift region 54, the substantially contiguous mass of engagement members can extend along at least a minimum of about 51% of a total perimeter of the appointed lift region 54. Alternatively, the substantially contiguous mass of engagement members extend along at least about 53% of the total perimeter of the appointed lift region, and optionally, can extend along at least about 55% of the total perimeter of the appointed lift region to provide improved performance. In other aspects, the substantially contiguous mass of engagement members extend along a maximum of not more than about 80% of the total perimeter of the appointed lift region 54. Alternatively, the substantially contiguous mass of engagement members extend along not more than about 75% of the total perimeter of the appointed lift region, and optionally, extend along not more than about 70% of the total perimeter of the appointed lift region to provide improved performance.

As representatively shown in the examples of the illustrated configurations, the lift region 54 contains a plurality of engagement members 40 which have been substantially deactivated and rendered substantially non-engageable with the appointed second fastener component 72. In a particular aspect of the invention, at least a minimum of about 20% of the engagement members 40 in the lift region 54 have been substantially deactivated. Alternatively, at least about 35%, and optionally, at least about 50% of the engagement members 40 in the lift region 54 have been substantially deactivated. Desirably, a majority of the engagement members 40 in the lift region 54 have been substantially deactivated. In further aspects, at least about 80%, and optionally up to approximately 100% of the engagement members in the lift region 54 have been substantially deactivated or disabled to thereby render the engagement members substantially non-engaging with the appointed second fastener component 72 to provide improved performance.

In the representatively shown configurations of the invention, the engagement member substrate 56 can be provided by a hook material substrate. Additionally, the plurality of engagement members 40 can be provided by prong-type hook members, and the lift region 54 can contain a plurality of hook members which have been substantially deactivated and rendered substantially non-engageable with the appointed second fastener component provided by the illustrated loop material. For example, at least a minimum of about 20% of the engagement members 40 in the lift region 54 can be substantially deactivated. Alternatively, at least about 35%, and optionally, at least about 50% of the engagement members 40 in the lift region 54 can be substantially deactivated. Desirably, a majority of the engagement members 40 in the lift region 54 can be substantially deactivated. In further aspects, at least about 80%, and optionally up to approximately 100% of the engagement members in the lift region 54 can be substantially deactivated or disabled to thereby render the engagement members substantially non-engaging with the appointed second fastener component 72 to provide improved performance.

Various techniques can be employed to selectively deactivate or otherwise render inoperative the engagement members 40 which are located in the appointed lift region 54. The techniques can include a crushing, melting, covering, shaving or abrading of the engagement members, or a filling-in or covering of the spaces between the engagement members, as well as combinations thereof. The melting may, for example, be produced by contact with a heated nip or ultrasonic bonder. The shaving may be produced by a knife or hot knife, and the abrading may be produced by a knurled device, a hot knurled device or sand paper surfaced device. The filling-in may include a filling with a material such as polymer or adhesive, and the covering may include a covering with film or fabric.

The deactivation of the engagement members 40 may be provided in a continuous or non-continuous pattern. Such patterns may include, for example, checkerboard patterns, dot patterns, patterns of stripes, patterns of wavy lines, arrangements of characters or figures, arrangements of logos, arrangements of geometric figures and the like, as well as combinations thereof. The geometric figures may include but are not limited to triangles, rectangles, polygons, ellipses, circles and the like, as well as combinations thereof.

The lift region 54 employed in the various configurations of the invention, such as the shown corner lift region or the pocket-shaped, indented lift region, can have a substantially continuous lateral extent 76 of at least a minimum of about 3 mm along the transverse, cross-direction 24 of the engagement member substrate 56. Alternatively, the lift region 54 can have a substantially continuous lateral extent of at least about 6 mm, and optionally, the lift region can have a substantially continuous lateral extent of at least about 9 mm along the transverse direction of the engagement member substrate. In other aspects, the lift region 54 can have a substantially continuous lateral extent 76 of not more than about 19 mm along the transverse direction 24 of the engagement member substrate 56. Alternatively, the lift region can have a substantially continuous lateral extent of not more than about 16 mm, and optionally, the lift region can have a substantially continuous lateral extent of not more than about 13 mm along the transverse direction of the engagement member substrate to provide improved performance.

In the various arrangements, a plurality of active engagement members are desirably positioned immediately adjacent to a laterally inboard edge of the lift region 54. With regard to the indented-type lift region 54, the area of the lift region 54 can project laterally inboard from the outboard edge region 90 of the engagement member substrate 56 by a depth distance which corresponds to the above-described lateral extent 76.

The lift region 54 employed in the various configurations of the invention, such as the shown corner-type lift region or the indented-type lift region, can also have a substantially continuous longitudinal extent 78 of at least a minimum of about 3 mm along a longitudinally extending, outboard edge 90 of the engagement member substrate 56. Alternatively, the lift region 54 can have a substantially continuous longitudinal extent of at least about 6 mm, and optionally, the lift region can have a substantially continuous longitudinal extent of at least about 9 mm along the outboard edge 90 of the engagement member substrate. In other aspects, the lift region 54 can have a substantially continuous longitudinal extent of not more than about 52 mm along the outboard edge 90 of the engagement member substrate 56. Alternatively, the lift region can have a substantially continuous longitudinal extent of not more than about 45 mm, and optionally, the lift region can have a substantially continuous longitudinal extent of not more than about 38 mm along the outboard edge 90 of the engagement member substrate to provide improved performance.

With reference again to FIGS. 4 through 4B, the corner-type lift region 54 can have a substantially continuous longitudinal extent 78 of not more than about 30 mm along the outboard edge 90 of the engagement member substrate 56. Alternatively, the lift region can have a substantially continuous longitudinal extent of not more than about 22 mm, and optionally, the lift region can have a substantially continuous longitudinal extent of not more than about 15 mm along the outboard edge 90 of the engagement member substrate to provide improved performance.

With reference to FIGS. 9 through 9B, the indented-type lift region 54 can have a substantially continuous longitudinal extent 78 of not more than about 52 mm along the outboard edge 90 of the engagement member substrate 56. Alternatively, the lift region can have a substantially continuous longitudinal extent of not more than about 45 mm, and optionally, the lift region can have a substantially continuous longitudinal extent of not more than about 38 mm along the outboard edge 90 of the engagement member substrate to provide improved performance.

In particular aspects of the indented-type lift region 54, the engagement member substrate layer 56 can have an overall outboard base length 98, and the lift region 54 can have a comparatively smaller longitudinal length 78, as representatively shown in FIG. 9. The outboard border length 100 of the lift region 54 can be not more than a maximum of about 95% of the outboard base length 98 of the engagement member substrate 56. The outboard border length 100 of the lift region can be not more than about 80%, and optionally can be not more than about 65% of the outboard base length 98 of the engagement member substrate to provide improved benefits. Accordingly, a sufficient area and number of operative engagement members in the bracketing arm sections 80 of the primary engagement section 52 can remain to secure and fasten the longitudinally opposed, arm sections of the primary engagement section 52 adjacent to the lift region 54 during ordinary use. In other aspects, the longitudinal length along the laterally outboard terminal edge of each securing arm section 80 can be at least a minimum of about 3 mm. Alternatively, the laterally outboard terminal edge of each arm section can have a longitudinal length of at least 6 mm, and optionally, the laterally outboard terminal edge of each arm section can have a longitudinal length of at least about 9 mm to provide an improved combination of securement and ease of removal.

In a further aspect of the invention, the lift region 54 can provide a lift area of at least a minimum of about 5 mm$^2$. Alternatively, the lift region can provide a lift area of at least about 25 mm$^2$, and optionally, can provide a lift area of at least about 35 mm$^2$ to provide improved performance. In other aspects, the lift region 54 can provide a lift area of not more than a maximum of about 1000 mm$^2$. Alternatively, the lift region can provide a lift area of not more than about 900 mm$^2$, and optionally, can provide a lift area of not more than about 800 mm$^2$ to provide desired benefits.

With regard to the corner-type of lift region 54, the lift region 54 can provide a lift area of at least a minimum of about 5 mm$^2$. Alternatively, the lift region can provide a lift area of at least about 25 mm$^2$, and optionally, can provide a lift area of at least about 35 mm$^2$ to provide improved performance. In other aspects, the lift region 54 can provide a lift area of not more than a maximum of about 750 mm$^2$. Alternatively, the lift region can provide a lift area of not more than about 400 mm$^2$, and optionally, can provide a lift area of not more than about 100 mm$^2$ to provide desired benefits.

With regard to particular aspects of the indented-type of lift region 54, the lift region can provide a lift area of at least a minimum of about 20 mm$^2$. Alternatively, the lift region can provide a lift area of at least about 50 mm$^2$, and optionally, can provide a lift area of at least about 90 mm$^2$ to provide improved performance. In other aspects, the lift region 54 can provide a lift area of not more than a maximum of about 1000 mm$^2$. Alternatively, the lift region can provide a lift area of not more than about 600 mm$^2$, and optionally, can provide a lift area of not more than about 200 mm$^2$ to provide desired benefits.

Figure 11:
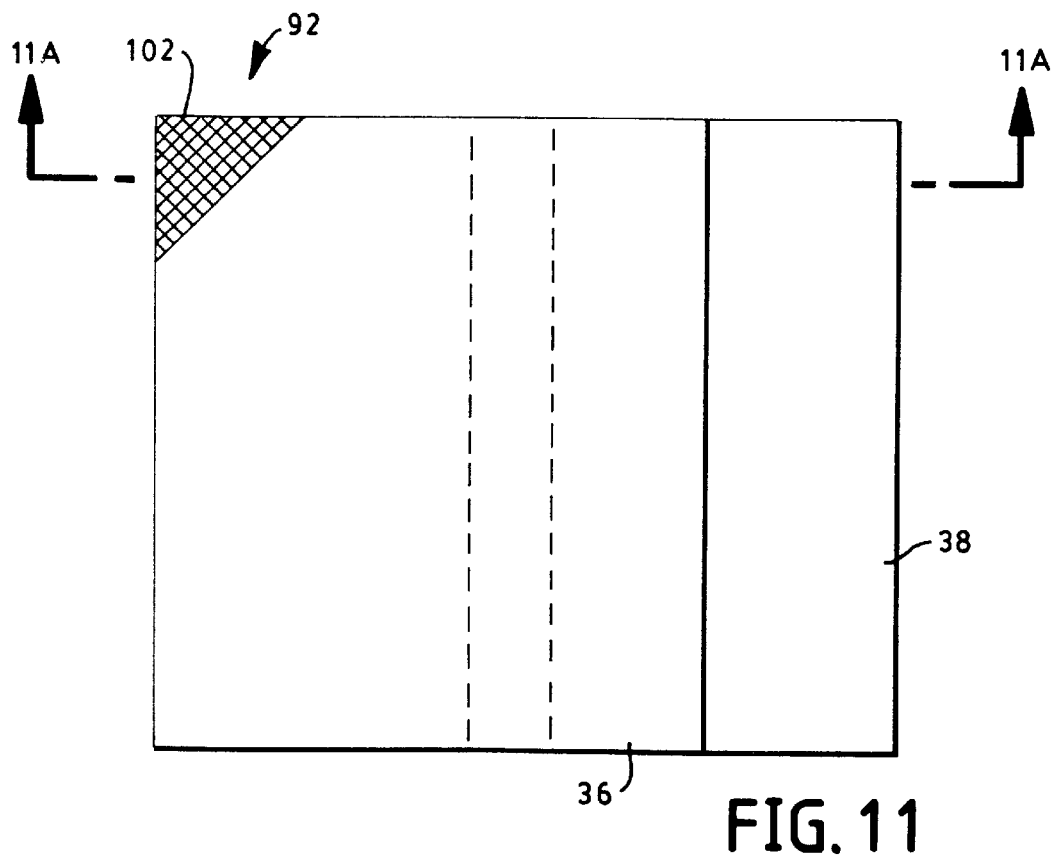
FIG. 11 representatively shows a fastening tab of the invention having a lift region indicator positioned on an outward side of the fastening tab.
Figure 11A:
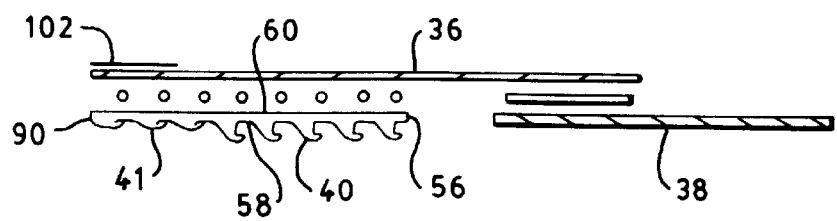
FIG. 11A representatively shows a schematic, laterally extending, expanded edge view along line 11A—11A of the fastening tab assembly illustrated in FIG. 11.

With reference to FIGS. 11 and 11A, the article can further include an indicator 102 positioned at the lift region 54. In a particular aspect, the fastener can, for example, be configured with a base color, and the lift region 54 can be designated by a supplemental color which visually differs from the base color. In another aspect, the fastener 36 can be configured to provide a primary, base tactile field, and the indicator 102 can be configured to provide a different, second tactile feel. The tactile feel differences can, for example, include softer/scratchier, smoother/rougher, thicker/thinner, more flexible/stiffer and sticky/less sticky, as well as combinations thereof.

In the various configurations of the invention, the desired first fastener component 70 can be a hook material which provides hook-type engagement members. An example of a suitable hook material is a micro-hook material which is distributed under the designation VELCRO HTH 829, and is available from VELCRO U.S.A., Inc., a business having offices in Manchester, N.H. The micro-hook material can have hooks in the shape of angled hook elements, and can be configured with a hook density of about 264 hooks per square centimeter (about 1700 hooks per square inch); a hook height which is within the range of about 0.030–0.063 cm (about 0.012–0.025 inch); and a hook width which is within the range of about 0.007 to 0.022 cm (about 0.003 to 0.009 inch). The hook elements are coextruded with a base layer substrate having a thickness of about 0.0076–0.008 cm (about 0.003–0.0035 inch), and the member of hook material has a Gurley stiffness of about 12 mgf (about 12 Gurley units). Other suitable hook materials can include VELCRO HTH 858, VELCRO HTH 851 and VELCRO HTH 863 hook materials.

For the purposes of the present invention, the various stiffness values are determined with respect to a bending moment produced by a force which is directed perpendicular to the plane substantially defined by the length and width of the component being tested. A suitable technique for determining the stiffness values described herein is a Gurley Stiffness test, a description of which is set forth in TAPPI Standard Test T 543 om-94 (Bending Resistance of Paper (Gurley type tester)). A suitable testing apparatus is a Gurley Digital Stiffness Tester; Model 4171-D manufactured by Teledyne Gurley, a business having offices in Troy, N.Y. For purposes of the present description, the stated Gurley stiffness values are intended to correspond to the values that would be generated by a "standard" sized sample. Accordingly, the scale readings from the Gurley stiffness tester are appropriately converted to the stiffness of a standard size sample, and are traditionally reported in terms of milligrams of force (mgf). Currently, a standard "Gurley unit" is equal to a stiffness value of 1 mgf, and may equivalently be employed to report the Gurley stiffness.

In the various configurations of the invention, the first mechanical fastener component 70, such as the shown hook material, can include a first substrate layer 56 having a substrate thickness, an engagement member surface 58, and an opposed substrate mounting surface 60. The selected engagement members, such as the shown hook members, are attached to the substrate layer 56, and project away from the engagement member surface 58. In particular aspects of the invention, the first, primary engagement section 52 and the lift region 54 can be formed or otherwise provided on substantially a single, unitary piece of the substrate layer 56. Thus, the appointed region of the substrate layer employed for the primary engagement section 52 is substantially contiguous with the appointed region of the substrate layer employed for the lift region 54. Alternatively, the primary engagement section 52 and the lift region 54 can be formed or otherwise provided on individual, separately provided sections or pieces of the substrate layer material.

In the various aspects of the invention the distribution patterns of the engagement members and the alignment patterns of the associated securement elements and engagement openings are determined with respect to the first fastener component prior to its engagement to the appointed, complementary second fastener component. In desired aspects, the distribution patterns and alignment patterns are substantially maintained when the first and second fastener components are operatively inter-engaged. In addition, the individual engagement members are typically flexible and resilient, but will substantially retain their initial shape during ordinary use. When flexed or deformed during ordinary use, the engagement members will substantially avoid plastically deforming to sustain the deformation, and will, instead, substantially return or "spring-back" to their original orientations and shape.

In the various aspects and configurations of the invention, the loop material can be provided by a nonwoven, woven or knit fabric. For example, a suitable loop material fabric can be composed of a 2 bar, warp knit fabric of the type available from Guilford Mills, Inc., Greensboro, N.C. under the trade designation #34285, as well other of knit fabrics. Suitable loop materials are also available from the 3M Company, which has distributed a nylon woven loop under their SCOTCHMATE brand. The 3M Company has also distributed a linerless loop web with adhesive on the backside of the web, and 3M knitted loop tape.

The loop material may also include a nonwoven fabric having continuous bonded areas defining a plurality of discrete unbonded areas. The fibers or filaments within the discrete unbonded areas of the fabric are dimensionally stabilized by the continuous bonded areas that encircle or surround each unbonded area, such that no support or backing layer of film or adhesive is required. The unbonded areas are specifically designed to afford spaces between fibers or filaments within the unbonded area that remain sufficiently open or large to receive and engage hook elements of the complementary hook material. In particular, a pattern-unbonded nonwoven fabric or web may include a spunbond nonwoven web formed of single component or multi-component melt-spun filaments. At least one surface of the nonwoven fabric can include a plurality of discrete, unbonded areas surrounded or encircled by continuous bonded areas. The continuous bonded areas dimensionally stabilize the fibers or filaments forming the nonwoven web boy bonding or fusing together the portions of the fibers or filaments that extend outside of the unbonded areas into the bonded areas, while leaving the fibers or filaments within the unbonded areas substantially free of bonding or fusing. The degree of bonding or fusing within the bonding areas desirably is sufficient to render the nonwoven web non-fibrous within the bonded areas, leaving the fibers or filaments within the unbonded areas to act as "loops" for receiving and engaging hook elements. Examples of suitable point-unbonded fabrics are described in U.S. patent application Ser. No. 754,419 entitled PATTERN-UNBONDED NONWOVEN WEB AND PROCESS FOR MAKING THE SAME, by T. J. Stokes et al., and filed Dec. 17, 1996 (attorney docket No. 12,232); the entire disclosure of which is incorporated herein by reference in a manner that is consistent herewith.

In the various configurations of the invention, the loop material need not be limited to a discrete or isolated patch on the outward surface of the article. Instead, the loop material can be provided by a substantially continuous, outer fibrous layer which is assembled, integrated or otherwise joined to extend over a predetermined surface area of the desired article. For example, the outer fibrous layer may be arranged to extend over substantially the total exposed surface area of a cloth-like outer cover employed with the article.

In the various arrangements of the invention, the engagement force between the selected first fastener component and its appointed and cooperating second fastener component should be large enough and durable enough to provide an adequate securement of the article on the wearer during use. In particular arrangements, especially where there are sufficiently high levels of engagement shear force provided by the fastening system, the fastening engagement may provide a peel force value of not less than a minimum of about 40 grams-force (gmf) per inch of the "width" of engagement between the first and second fastener components. In further arrangements, the fastening engagement may provide a peel force value of not less than about 100 gmf/inch to provide improved advantages. In desired configurations, the fastening engagement may provide a peel force value of not less than about 200 gmf per inch of the "width" of engagement between the first and second fastener components. Alternatively, the peel force is not less than about 300 gmf/inch, and optionally is not less than about 400 gmf/inch to further provide improved benefits. In other aspects, the peel force is not more than about 1,200 gmf/inch. Alternatively, the peel force is not more than about 800 gmf/inch, and optionally is not more than about 600 gmf/inch to provide improved performance.

The engagement force between the selected first fastener component and its appointed and cooperating second fastener component may additionally provide a shear force value of not less than about 400 gmf per square inch of the area of engagement between the first and second fastener components. Alternatively, the shear force is not less than about 1,000 gmf/in$^2$, and optionally, is not less than about 1,700 gmf/in$^2$. In further aspects, the shear force can be up to about 4,400 gmf/in$^2$, or more. Alternatively, the shear force is not more than about 3,900 gmf/in$^2$, and optionally is not more than about 3,500 gmf/in$^2$ to provide improved performance.

The peel force value can be determined in accordance with standard procedure ASTM D5170, approved Sep. 15, 1991 and published Nov. 1991; with the following particulars. The test specimen is the fastener tab from the article being assessed. The test specimen length is the dimension aligned along the direction in which a peel-away force is typically applied to disengage and remove the fastener during the ordinary use of the article with which the fastener is employed. The specimen "width" lies within the general plane of the fastener and is perpendicular to the specimen length. The roller device weighs 4.5 pounds and includes a rubber coating around the roller circumference. A suitable roller is part number HR-100 available from Chemsultants International, a business having a location in Mentor, Ohio. During the engagement of the fastener components, the roller is rolled over the test specimen through one cycle in the direction of the cross-wise "width" of the sample. In addition, the initial peel by hand to "raise the loops" is omitted. During testing, the fastener material held by the stationary clamp can be larger in area, as compared to the fastener material held in the moving clamp. The initial separation distance between the clamps of the tensile tester is 4 inch, and the extension speed of the tensile testing machine is 20 inch/min. The reported value of a peel test result is a "three-peak average" value employing MTS TESTWORKS software with a peak criteria of 2%. Additionally, the peel force value is normalized to be stated in terms of force per unit length of the "width" dimension of the fastener component on the test specimen, such as grams per inch. The MTS TESTWORKS software is available from MTS Systems Corporation, a business having offices in Eden Prairie, Minn.

The shear force value can be determined in accordance with the standard procedure ASTM D-5169, approved Sep. 15, 1991 and published Nov. 1991 with the following particulars. The test specimen is composed of the fastener tab from the article being assessed. The test specimen length and width typically correspond to the length and width employed to conduct the testing for peel force value. Ordinarily, the test specimen length is the dimension aligned along the direction in which a shear force is typically applied to the fastener during the ordinary use of the article with which the fastener is employed. The specimen "width" lies within the general plane of the fastener and is perpendicular to the specimen length. The roller device weighs 4.5 pounds and includes a rubber coating around the roller. A suitable roller is part number HR-100 available from Chemsultants International, a business having a location in Mentor, Ohio. During the engagement of the fastener components, the roller is rolled over the test specimen through five cycles in the direction of the cross-wise "width" of the sample. In addition, the initial peel by hand to "raise the loops" is omitted. During testing, the fastener material (e.g. the loop material) held by the stationary clamp can be larger in area, as compared to the fastener material (e.g. hook material) held in the moving clamp. The initial separation distance between the clamps of the tensile tester is 4 inch, and the extension speed of the tensile testing machine is 10 inch/min. The shear force value is normalized to be stated in terms of force per unit area of the test specimen, such as grams per inch$^2$.

The particulars of the standard test procedures are intended to generate fastening conditions that can be more representative of consumer use conditions. When preparing the test specimen materials (e.g. hook and loop materials) to determine the cooperating peel and/or shear force values for the representatively shown configurations of the invention, it should be noted that, the width dimension of the selected specimen material will correspond to the dimension of the fastener material which, in the actual article, is found to be aligned along the longitudinal direction 26 of the article. Similarly, the length dimension of the selected specimen material will correspond to the dimension of the fastener material which, in the actual article, is found to be aligned along the lateral direction 24 of the article.

Desirably, the securing engagement between the first and second fastener components should be sufficient to prevent a disengagement of the fastener tab 36 away from the landing member 50 when the fastener tab 36 is subject to a tensile force of at least about 1,000 grams when the tensile force is applied outwardly along the lateral direction, aligned generally parallel with the plane of the backsheet layer 30 of the article.

Each of the fastener components and fastening elements in the various constructions of the invention may be operably attached to its supporting substrate by employing any one or more of the attachment mechanisms employed to construct and hold together the various other components of the article of the invention. The fastening elements in the various fastening regions, may be integrally formed, such as by molding, co-extrusion or the like, along with their associated substrate layer. The substrate layer and its associated mechanical fastening elements may be formed from substantially the same polymer material, and there need not be a discrete step of attaching the fastening elements to an initially separate substrate layer. For example, the individual hook elements may be integrally formed simultaneously with a hook base-layer by coextruding the base layer and hook elements from substantially the same polymer material.

It should be readily appreciated that the strength of the attachment or other interconnection between the substrate layer and the attached fastening component should be greater than the peak force required to remove the fastener tab 36 from its releasable securement to the appointed landing member of the article.

Having described the invention in rather full detail, it will be readily apparent that various changes and modifications can be made without departing from the spirit of the invention. All of such changes and modifications are contemplated as being within the scope of the invention as defined by the subjoined claims.

We claim:

1. An article having a lengthwise longitudinal direction and a lateral cross-direction, said article comprising: a first article portion; a second article portion; and a fastener for securing said first article portion to said second article portion;

said fastener including
  at least one first fastener component attached to a lateral side section of said first article portion, and
  a cooperating, second fastener component which is mechanically interengageable with said first fastener component and is attached to said second article portion;

said first fastener component including
  an engagement substrate having an appointed lift region, and
  a plurality of engagement members operably attached to extend away from said engagement substrate; wherein
  said lift region is restricted to only a limited portion of a longitudinally extending, outboard border edge of said engagement substrate,
  said lift region contains a plurality of engagement members which have a substantially deactivated configuration.

2. An article as recited in claim 1, wherein a majority of said engagement members in said lift region have said substantially deactivated configuration.

3. An article as recited in claim 1, wherein at least about 20% of said engagement members in said lift region have said substantially deactivated configuration.

4. An article as recited in claim 1, wherein
  said engagement substrate is provided by hook material substrate;
  said plurality of engagement members are provided by hook members; and
  said lift region contains a plurality of hook members which have said substantially deactivated configuration.

5. An article as recited in claim 4, wherein at least about 20% of said hook members in said lift region have said substantially deactivated configuration.

6. An article as recited in claim 1, wherein said lift region has a continuous lateral extent of at least a minimum of about 3 mm along said engagement substrate.

7. An article as recited in claim 6, wherein said lift region provides a lift area of at least about 5 mm$^2$.

8. An article as recited in claim 6, wherein said lift region has a continuous longitudinal extent of at least about 3 mm along an outboard edge of the engagement substrate.

9. An article as recited in claim 1, wherein said lift region has a lift area of at least about 5 mm$^2$ and not more than about 1000 mm$^2$.

10. An article as recited in claim 4, wherein said substrate of hook material includes an outboard, distal corner portion, and said lift region is restricted to said outboard corner portion.

11. An article as recited in claim 4, wherein said substrate of hook material includes a laterally outboard, distal border portion; and said lift region is restricted to a limited portion of a medial section of said outboard border portion.

12. An article as recited in claim 4, wherein a plurality of active hook members are positioned immediately adjacent to a laterally inboard edge of said lift region; and said lift region extends laterally inboard from said outboard edge of the engagement substrate by a depth distance which is not more than a maximum of about 19 mm and is at least a minimum of about 3 mm.

13. An article as recited in claim 4, wherein said substrate of hook material has an outboard base length, and said lift region has a longitudinal length, said longitudinal length of the lift region being not more than about 95% of said outboard base length of the substrate of hook material.

14. An article as recited in claim 4, further comprising an indicator positioned at said lift region.

15. An article as recited in claim 14, wherein said fastener is configured with a base color, and said lift region designated by a supplemental color which visually differs from said base color.

16. An article as recited in claim 14, wherein said fastener provides a primary, base tactile feel, and said indicator is a tactile indicator which provides a different, second tactile feel.

17. An article as recited in claim 1, wherein said first article portion provides a first waistband portion, said second article portion provides a second waistband portion, said article includes an intermediate portion which interconnects said first and second waistband portions; and wherein said article further comprises: a backsheet layer; a liquid-permeable topsheet layer; and an absorbent body sandwiched between said backsheet layer and topsheet layer.

18. An article as recited in claim 1, wherein said engagement substrate includes an outboard, distal corner portion, and said lift region is restricted to said outboard, distal corner portion.

19. An article as recited in claim 1, wherein said engagement substrate includes a laterally outboard, distal border portion; and said lift region is restricted to a limited portion of a medial section if said laterally outboard, distal border portion.

20. An article as recited in claim 11, wherein said substrate of hook material includes bracketing arm sections for securing longitudinally opposed sections of the hook material that are adjacent said lift region.

* * * * *

UNITED STATES PATENT AND TRADEMARK OFFICE
CERTIFICATE OF CORRECTION

PATENT NO.   : 6,210,389 B1  Page 1 of 1
DATED        : April 3, 2001
INVENTOR(S)  : Andrew Mark Long, Patrick Robert Lord, Brian Keith Nortman, Paula Kay Zoromski, Richard John Schmidt and Mari-Pat Yvonne Von Feldt It is certified that error appears in the above-identified patent and that said Letters Patent is hereby corrected as shown below:

<u>Column 5,</u>
Line 33, delete "posited" and substitute -- positioned --.

Signed and Sealed this

Twenty-third Day of July, 2002

*Attest:*

*Attesting Officer*

JAMES E. ROGAN
*Director of the United States Patent and Trademark Office*